(12) United States Patent
Nohr et al.

(10) Patent No.: US 6,265,458 B1
(45) Date of Patent: Jul. 24, 2001

(54) PHOTOINITIATORS AND APPLICATIONS THEREFOR

(75) Inventors: Ronald S. Nohr, Alpharetta; John Gavin MacDonald, Decatur, both of GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/407,007

(22) Filed: Sep. 28, 1999

(51) Int. Cl.[7] ................................................... C08F 2/48
(52) U.S. Cl. ............................. 522/6; 522/1; 522/49; 522/50; 522/51; 522/53; 522/63; 522/66
(58) Field of Search ........................ 522/1, 6, 49, 50, 522/51, 53, 63, 66

(56) References Cited

U.S. PATENT DOCUMENTS

| | | |
|---|---|---|
| Re. 28,225 | 11/1974 | Heseltine et al. . |
| Re. 28,789 | 4/1976 | Chang . |
| 575,228 | 1/1897 | von Gallois . |
| 582,853 | 5/1897 | Feer . |
| 893,636 | 7/1908 | Maywald . |
| 1,013,544 | 1/1912 | Fuerth . |
| 1,325,971 | 12/1919 | Akashi . |
| 1,364,406 | 1/1921 | Olsen . |
| 1,436,856 | 11/1922 | Brenizer et al. . |
| 1,744,149 | 1/1930 | Staehlin . |
| 1,803,906 | 5/1931 | Krieger et al. . |
| 1,844,199 | 2/1932 | Bicknell et al. . |
| 1,876,880 | 9/1932 | Drapal . |
| 1,880,572 | 10/1932 | Wendt et al. . |
| 1,880,573 | 10/1932 | Wendt et al. . |
| 1,916,350 | 7/1933 | Wendt et al. . |
| 1,916,779 | 7/1933 | Wendt et al. . |
| 1,955,898 | 4/1934 | Wendt et al. . |
| 1,962,111 | 6/1934 | Bamberger . |
| 2,005,378 | 6/1935 | Kiel . |
| 2,005,511 | 6/1935 | Stoll et al. . |
| 2,049,005 | 7/1936 | Gaspar . |
| 2,054,390 | 9/1936 | Rust et al. . |
| 2,058,489 | 10/1936 | Murch et al. . |
| 2,062,304 | 12/1936 | Gaspar . |
| 2,090,511 | 8/1937 | Crossley et al. . |
| 2,097,119 | 10/1937 | Eggert . |
| 2,106,539 | 1/1938 | Schnitzspahn . |
| 2,111,692 | 3/1938 | Saunders et al. . |
| 2,125,015 | 7/1938 | Gaspar . |
| 2,130,572 | 9/1938 | Wendt . |
| 2,132,154 | 10/1938 | Gaspar . |
| 2,145,960 | 2/1939 | Wheatley et al. . |
| 2,154,996 | 4/1939 | Rawling . |
| 2,159,280 | 5/1939 | Mannes et al. . |
| 2,171,976 | 9/1939 | Erickson . |
| 2,181,800 | 11/1939 | Crossley et al. . |
| 2,185,153 | 12/1939 | Lecher et al. . |
| 2,220,178 | 11/1940 | Schneider . |
| 2,230,590 | 2/1941 | Eggert et al. . |
| 2,237,885 | 4/1941 | Markush et al. . |

(List continued on next page.)

FOREIGN PATENT DOCUMENTS

| | | |
|---|---|---|
| 103085 | 4/1937 | (AU) . |
| 12624/88 | 9/1988 | (AU) . |
| 620075 | 5/1962 | (BE) . |
| 637169 | 3/1964 | (BE) . |

(List continued on next page.)

OTHER PUBLICATIONS

Noguchi, H. UV Curable, Aqueous Ink Jet Ink: Material Design and Performance for Digital Printing *1998 International Conf. on Digital Printing Technologies* 107–110.
ESP@CENET databse JP 10324836 (Omron Corp.), Dec. 8, 1998. abstract.
Derwent World Patents Index JP 8002092 (Mitsubishi Paper Mills Ltd.) Jan. 9, 1996. abstract.
Kubat et al. "Photophysical properties of metal complexes of meso–tetrakis (40sulphonatophenyl) porphyrin," *J. Photochem. and Photobiol.* 96 93–97 1996.
Derwent World Patents Index EP 659039 (Canon KK) Jun. 21, 1995 abstract.
Derwent World Patents Index JP 7061114 (Dainippon Printing Co. Ltd.) Mar. 7, 1995. abstract.
Abstract for WO 95/00343—A1 *Textiles: Paper: Cellulose* p. 7 1995.

(List continued on next page.)

*Primary Examiner*—James J. Seidleck
*Assistant Examiner*—Sanza McClendon
(74) *Attorney, Agent, or Firm*—Kilpatrick Stockton LLP

(57) ABSTRACT

The present invention is directed to new, energy-efficient, photoinitiators having the following general formula:

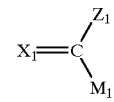

wherein of $X_1$ is a conjugated system such as one or more aryl groups or substituted aryl groups; $Z_1$ is —O, —S, an alkyl group having from one to six carbon atoms, an ester moiety, a ketone moiety, an amine moiety, an imine moiety, an ether moiety, an aryl or substituted aryl group, a metal or non-metal, or a metal or non-metal containing group, such as a zinc-containing group or a boron-containing group, respectively; and $M_1$ is an alkyl group, a substituted alkyl group, or forms a five-member ring with $Z_1$. The present invention is also directed to a method of generating a reactive species, which includes exposing one or more photoinitiators to radiation to form one or more reactive species. Also described are methods of polymerizing polymerizable materials, methods of curing an unsaturated oligomer/monomer mixture, and methods of laminating using the photoinitiators of the present invention. In addition, the present invention is directed to ink compositions, adhesive compositions and resins, and methods of printing using the above-described photoinitiators.

17 Claims, No Drawings

U.S. PATENT DOCUMENTS

| | | |
|---|---|---|
| 2,243,630 | 5/1941 | Houk et al. . |
| 2,268,324 | 12/1941 | Polgar . |
| 2,281,895 | 5/1942 | van Poser et al. . |
| 2,328,166 | 8/1943 | Poigar et al. . |
| 2,346,090 | 4/1944 | Staehle . |
| 2,349,090 | 5/1944 | Haddock . |
| 2,356,618 | 8/1944 | Rossander et al. . |
| 2,361,301 | 10/1944 | Libby, Jr. et al. . |
| 2,364,359 | 12/1944 | Kienle et al. . |
| 2,381,145 | 8/1945 | von Glahn et al. . |
| 2,382,904 | 8/1945 | Federsen . |
| 2,386,646 | 10/1945 | Adams et al. . |
| 2,402,106 | 6/1946 | von Glahn et al. . |
| 2,416,145 | 2/1947 | Biro . |
| 2,477,165 | 7/1949 | Bergstrom . |
| 2,527,347 | 10/1950 | Bergstrom . |
| 2,580,461 | 1/1952 | Pearl . |
| 2,601,669 | 9/1952 | Tullsen . |
| 2,612,494 | 9/1952 | von Glahn et al. . |
| 2,612,495 | 9/1952 | von Glahn et al. . |
| 2,628,959 | 2/1953 | von Glahn et al. . |
| 2,647,080 | 7/1953 | Joyce . |
| 2,680,685 | 6/1954 | Ratchford . |
| 2,728,784 | 12/1955 | Tholstrup et al. . |
| 2,732,301 | 1/1956 | Robertson et al. . |
| 2,744,103 | 5/1956 | Koch . |
| 2,757,090 | 7/1956 | Meugebauer et al. . |
| 2,763,550 | 9/1956 | Lovick . |
| 2,768,171 | 10/1956 | Clarke et al. . |
| 2,773,056 | 12/1956 | Helfaer . |
| 2,798,000 | 7/1957 | Monterman . |
| 2,809,189 | 10/1957 | Stanley et al. . |
| 2,827,358 | 3/1958 | Kaplan et al. . |
| 2,834,773 | 5/1958 | Scalera et al. . |
| 2,875,045 | 2/1959 | Lurie . |
| 2,892,865 | 6/1959 | Giraldi et al. . |
| 2,897,187 | 7/1959 | Koch . |
| 2,936,241 | 5/1960 | Sharp et al. . |
| 2,940,853 | 6/1960 | Sagura et al. . |
| 2,955,067 | 10/1960 | McBurney et al. . |
| 2,992,129 | 7/1961 | Gauthier . |
| 2,992,198 | 7/1961 | Funahasi . |
| 3,030,208 | 4/1962 | Schellenberg et al. . |
| 3,071,815 | 1/1963 | MacKinnon . |
| 3,075,014 | 1/1963 | Palopoli et al. . |
| 3,076,813 | 2/1963 | Sharp . |
| 3,104,973 | 9/1963 | Sprague et al. . |
| 3,114,634 | 12/1963 | Brown et al. . |
| 3,121,632 | 2/1964 | Sprague et al. . |
| 3,123,647 | 3/1964 | Duennenberger et al. . |
| 3,133,049 | 5/1964 | Hertel et al. . |
| 3,140,949 | 7/1964 | Sprague et al. . |
| 3,154,416 | 10/1964 | Fidelman . |
| 3,155,509 | 11/1964 | Roscow . |
| 3,175,905 | 3/1965 | Wiesbaden . |
| 3,178,285 | 4/1965 | Anderau et al. . |
| 3,238,163 | 3/1966 | O'Neill . |
| 3,242,215 | 3/1966 | Heitmiller . |
| 3,248,337 | 4/1966 | Zirker et al. . |
| 3,266,973 | 8/1966 | Crowley . |
| 3,282,886 | 11/1966 | Gadecki . |
| 3,284,205 | 11/1966 | Sprague et al. . |
| 3,300,314 | 1/1967 | Rauner et al. . |
| 3,304,297 | 2/1967 | Wegmann et al. . |
| 3,305,361 | 2/1967 | Gaynor et al. . |
| 3,313,797 | 4/1967 | Kissa . |
| 3,320,080 | 5/1967 | Mazzarella et al. . |
| 3,330,659 | 7/1967 | Wainer . |
| 3,341,492 | 9/1967 | Champ et al. . |
| 3,359,109 | 12/1967 | Harder et al. . |
| 3,361,827 | 1/1968 | Biletch . |
| 3,363,969 | 1/1968 | Brooks . |
| 3,385,700 | 5/1968 | Willems et al. . |
| 3,397,984 | 8/1968 | Williams et al. . |
| 3,415,875 | 12/1968 | Luethi et al. . |
| 3,418,118 | 12/1968 | Thommes et al. . |
| 3,445,234 | 5/1969 | Cescon et al. . |
| 3,453,258 | 7/1969 | Parmerter et al. . |
| 3,453,259 | 7/1969 | Parmerter et al. . |
| 3,464,841 | 9/1969 | Skofronick . |
| 3,467,647 | 9/1969 | Benninga . |
| 3,479,185 | 11/1969 | Chambers . |
| 3,502,476 | 3/1970 | Kohei et al. . |
| 3,503,744 | 3/1970 | Itano et al. . |
| 3,514,597 | 5/1970 | Haes et al. . |
| 3,541,142 | 11/1970 | Cragoe, Jr. . |
| 3,546,161 | 12/1970 | Wolheim . |
| 3,547,646 | 12/1970 | Hori et al. . |
| 3,549,367 | 12/1970 | Chang et al. . |
| 3,553,710 | 1/1971 | Lloyd et al. . |
| 3,563,931 | 2/1971 | Horiguchi . |
| 3,565,753 | 2/1971 | Yurkowitz . |
| 3,574,624 | 4/1971 | Reynolds et al. . |
| 3,579,533 | 5/1971 | Yalman . |
| 3,595,655 | 7/1971 | Robinson et al. . |
| 3,595,657 | 7/1971 | Robinson et al. . |
| 3,595,658 | 7/1971 | Gerlach et al. . |
| 3,595,659 | 7/1971 | Gerlach et al. . |
| 3,607,639 | 9/1971 | Krefeld et al. . |
| 3,607,693 | 9/1971 | Heine et al. . |
| 3,607,863 | 9/1971 | Dosch . |
| 3,615,562 | 10/1971 | Harrison et al. . |
| 3,617,288 | 11/1971 | Hartman et al. . |
| 3,617,335 | 11/1971 | Kumura et al. . |
| 3,619,238 | 11/1971 | Kimura et al. . |
| 3,619,239 | 11/1971 | Osada et al. . |
| 3,637,337 | 1/1972 | Pilling . |
| 3,637,581 | 1/1972 | Horioguchi et al. . |
| 3,642,472 | 2/1972 | Mayo . |
| 3,647,467 | 3/1972 | Grubb . |
| 3,652,275 | 3/1972 | Baum et al. . |
| 3,660,542 | 5/1972 | Adachi et al. . |
| 3,667,954 | 6/1972 | Itano et al. . |
| 3,668,188 | 6/1972 | King et al. . |
| 3,669,925 | 6/1972 | King et al. . |
| 3,671,096 | 6/1972 | Mackin . |
| 3,671,251 | 6/1972 | Houle et al. . |
| 3,676,690 | 7/1972 | McMillin et al. . |
| 3,678,044 | 7/1972 | Adams . |
| 3,689,565 | 9/1972 | Hoffmann et al. . |
| 3,694,241 | 9/1972 | Guthrie et al. . |
| 3,695,879 | 10/1972 | Laming et al. . |
| 3,697,280 | 10/1972 | Strilko . |
| 3,705,043 | 12/1972 | Zablak . |
| 3,707,371 | 12/1972 | Files . |
| 3,729,313 | 4/1973 | Smith . |
| 3,737,628 | 6/1973 | Azure . |
| 3,765,896 | 10/1973 | Fox . |
| 3,775,130 | 11/1973 | Enomoto et al. . |
| 3,788,849 | 1/1974 | Taguchi et al. . |
| 3,799,773 | 3/1974 | Watarai et al. . |
| 3,800,439 | 4/1974 | Sokolski et al. . |
| 3,801,329 | 4/1974 | Sandner et al. . |
| 3,817,752 | 6/1974 | Laridon et al. . |
| 3,840,338 | 10/1974 | Zviak et al. . |
| 3,844,790 | 10/1974 | Chang et al. . |
| 3,870,524 | 3/1975 | Watanabe et al. . |
| 3,873,500 | 3/1975 | Kato et al. . |
| 3,876,496 | 4/1975 | Lozano . |

| | | |
|---|---|---|
| 3,887,450 | 6/1975 | Gilano et al. . |
| 3,895,949 | 7/1975 | Akamatsu . |
| 3,901,779 | 8/1975 | Mani . |
| 3,904,562 | 9/1975 | Hopfenberg et al. . |
| 3,910,993 | 10/1975 | Avar et al. . |
| 3,914,165 | 10/1975 | Gaske . |
| 3,914,166 | 10/1975 | Rudolph et al. . |
| 3,915,824 | 10/1975 | McGinniss . |
| 3,919,323 | 11/1975 | Houlihan et al. . |
| 3,926,641 | 12/1975 | Rosen . |
| 3,928,264 | 12/1975 | Young, Jr. et al. . |
| 3,933,682 | 1/1976 | Bean . |
| 3,952,129 | 4/1976 | Matsukawa et al. . |
| 3,960,685 | 6/1976 | Sano et al. . |
| 3,965,157 | 6/1976 | Harrison . |
| 3,978,132 | 8/1976 | Houlihan et al. . |
| 3,984,248 | 10/1976 | Sturmer . |
| 3,988,154 | 10/1976 | Sturmer . |
| 4,004,998 | 1/1977 | Rosen . |
| 4,012,256 | 3/1977 | Levinos . |
| 4,017,652 | 4/1977 | Gruber . |
| 4,022,674 | 5/1977 | Rosen . |
| 4,024,324 | 5/1977 | Sparks . |
| 4,039,332 | 8/1977 | Kokelenberg et al. . |
| 4,043,819 | 8/1977 | Baumann . |
| 4,048,034 | 9/1977 | Martan . |
| 4,054,719 | 10/1977 | Cordes, III . |
| 4,056,665 | 11/1977 | Tayler et al. . |
| 4,058,400 | 11/1977 | Crivello . |
| 4,065,315 * | 12/1977 | Yamazaki et al. .................... 430/269 |
| 4,067,892 | 1/1978 | Thorne et al. . |
| 4,071,424 | 1/1978 | Dart et al. . |
| 4,073,968 | 2/1978 | Miyamoto et al. . |
| 4,077,769 | 3/1978 | Garcia . |
| 4,079,183 | 3/1978 | Green . |
| 4,085,062 | 4/1978 | Virgilio et al. . |
| 4,090,877 | 5/1978 | Streeper . |
| 4,100,047 | 7/1978 | McCarty . |
| 4,105,572 | 8/1978 | Gorondy . |
| 4,107,733 | 8/1978 | Schickedanz . |
| 4,110,112 | 8/1978 | Roman et al. . |
| 4,111,699 | 9/1978 | Krueger . |
| 4,114,028 | 9/1978 | Baio et al. . |
| 4,126,412 | 11/1978 | Masson et al. . |
| 4,132,562 | 1/1979 | Burke, Jr. et al. . |
| 4,141,807 | 2/1979 | Via . |
| 4,144,156 | 3/1979 | Kuesters et al. . |
| 4,148,658 | 4/1979 | Kondoh et al. . |
| 4,162,162 | 7/1979 | Dueber . |
| 4,171,977 | 10/1979 | Hasegawa et al. . |
| 4,179,577 | 12/1979 | Green . |
| 4,181,807 | 1/1980 | Green . |
| 4,189,323 * | 2/1980 | Burh ................................. 430/281.1 |
| 4,190,671 | 2/1980 | Vanstone et al. . |
| 4,197,080 | 4/1980 | Mee . |
| 4,199,420 | 4/1980 | Photis . |
| 4,212,970 * | 7/1980 | Iwasaki ................................. 548/143 |
| 4,229,172 | 10/1980 | Baumann et al. . |
| 4,232,106 | 11/1980 | Iwasaki et al. . |
| 4,234,106 * | 11/1980 | Rywak et al. .................... 222/239 |
| 4,238,492 | 12/1980 | Majoie . |
| 4,239,843 | 12/1980 | Hara et al. . |
| 4,239,850 | 12/1980 | Kita et al. . |
| 4,241,155 | 12/1980 | Hara et al. . |
| 4,242,430 | 12/1980 | Hara et al. . |
| 4,242,431 | 12/1980 | Hara et al. . |
| 4,245,018 | 1/1981 | Hara et al. . |
| 4,245,033 | 1/1981 | Eida et al. . |
| 4,245,995 | 1/1981 | Hugl et al. . |
| 4,246,330 | 1/1981 | Hara et al. . |
| 4,248,949 | 2/1981 | Hara et al. . |
| 4,250,096 | 2/1981 | Kvita et al. . |
| 4,251,622 | 2/1981 | Kimoto et al. . |
| 4,251,662 | 2/1981 | Ozawa et al. . |
| 4,254,195 | 3/1981 | Hara et al. . |
| 4,256,493 | 3/1981 | Yokoyama et al. . |
| 4,256,817 | 3/1981 | Hara et al. . |
| 4,258,123 | 3/1981 | Nagashima et al. . |
| 4,258,367 | 3/1981 | Mansukhani . |
| 4,259,432 | 3/1981 | Kondoh et al. . |
| 4,262,936 | 4/1981 | Miyamoto . |
| 4,268,605 | 5/1981 | Hara et al. . |
| 4,268,667 | 5/1981 | Anderson . |
| 4,269,926 | 5/1981 | Hara et al. . |
| 4,270,130 | 5/1981 | Houle et al. . |
| 4,271,252 | 6/1981 | Hara et al. . |
| 4,271,253 | 6/1981 | Hara et al . |
| 4,272,244 | 6/1981 | Schlick . |
| 4,276,211 | 6/1981 | Singer et al. . |
| 4,277,497 | 7/1981 | Fromantin . |
| 4,279,653 | 7/1981 | Makishima et al. . |
| 4,279,982 | 7/1981 | Iwasaki et al. . |
| 4,279,985 | 7/1981 | Nonogaki et al. . |
| 4,284,485 | 8/1981 | Berner . |
| 4,288,631 | 9/1981 | Ching . |
| 4,289,844 | 9/1981 | Specht et al. . |
| 4,290,870 | 9/1981 | Kondoh et al. . |
| 4,293,458 | 10/1981 | Gruenberger et al. . |
| 4,298,679 | 11/1981 | Shinozaki et al. . |
| 4,300,123 | 11/1981 | McMillin et al. . |
| 4,301,223 | 11/1981 | Nakamura et al. . |
| 4,302,606 | 11/1981 | Barabas et al. . |
| 4,306,014 | 12/1981 | Kunikane et al. . |
| 4,307,182 | 12/1981 | Dalzell et al. . |
| 4,308,400 | 12/1981 | Felder et al. . |
| 4,315,807 | 2/1982 | Felder et al. . |
| 4,318,705 | 3/1982 | Nowak et al. . |
| 4,318,791 | 3/1982 | Felder et al. . |
| 4,321,118 | 3/1982 | Felder et al. . |
| 4,335,054 | 6/1982 | Blaser et al. . |
| 4,335,055 | 6/1982 | Blaser et al. . |
| 4,336,323 | 6/1982 | Winslow . |
| 4,343,891 | 8/1982 | Aasen et al. . |
| 4,345,011 | 8/1982 | Drexhage . |
| 4,347,111 | 8/1982 | Gehlhaus et al. . |
| 4,349,617 | 9/1982 | Kawashiri et al. . |
| 4,350,753 | 9/1982 | Shelnut et al. . |
| 4,351,893 | 9/1982 | Anderson . |
| 4,356,255 | 10/1982 | Tachikawa et al. . |
| 4,357,468 | 11/1982 | Szejtli et al. . |
| 4,359,524 | 11/1982 | Masuda et al. . |
| 4,362,806 | 12/1982 | Whitmore . |
| 4,367,072 | 1/1983 | Vogtle et al. . |
| 4,367,280 | 1/1983 | Kondo et al. . |
| 4,369,283 | 1/1983 | Altschuler . |
| 4,370,401 | 1/1983 | Winslow et al. . |
| 4,372,582 | 2/1983 | Geisler . |
| 4,373,017 | 2/1983 | Masukawa et al. . |
| 4,373,020 | 2/1983 | Winslow . |
| 4,374,984 | 2/1983 | Eichler et al. . |
| 4,376,887 | 3/1983 | Greenaway et al. . |
| 4,383,835 | 5/1983 | Preuss et al. . |
| 4,390,616 | 6/1983 | Sato et al. . |
| 4,391,867 | 7/1983 | Derick et al. . |
| 4,399,209 | 8/1983 | Sanders et al. . |
| 4,400,173 | 8/1983 | Beavan . |
| 4,401,470 | 8/1983 | Bridger . |
| 4,416,961 | 11/1983 | Drexhage . |
| 4,421,559 | 12/1983 | Owatari . |
| 4,424,325 | 1/1984 | Tsunoda et al. . |
| 4,425,162 | 1/1984 | Sugiyama . |
| 4,425,424 | 1/1984 | Altland et al. . |

| Patent No. | Date | Inventor |
|---|---|---|
| 4,426,153 | 1/1984 | Libby et al. . |
| 4,434,035 | 2/1984 | Eichler et al. . |
| 4,440,827 | 4/1984 | Miyamoto et al. . |
| 4,447,521 | 5/1984 | Tiers et al. . |
| 4,450,227 | 5/1984 | Holmes et al. . |
| 4,460,676 | 7/1984 | Fabel . |
| 4,467,112 | 8/1984 | Matsuura et al. . |
| 4,475,999 | 10/1984 | Via . |
| 4,477,681 | 10/1984 | Gehlhaus et al. . |
| 4,489,334 | 12/1984 | Owatari . |
| 4,495,041 | 1/1985 | Goldstein . |
| 4,496,447 | 1/1985 | Eichler et al. . |
| 4,500,355 | 2/1985 | Shimada et al. . |
| 4,508,570 | 4/1985 | Fugii et al. . |
| 4,510,392 | 4/1985 | Litt et al. . |
| 4,523,924 | 6/1985 | Lacroix . |
| 4,524,122 | 6/1985 | Weber et al. . |
| 4,534,838 | 8/1985 | Lin et al. . |
| 4,537,855 * | 8/1985 | Ide .................................... 430/285.1 |
| 4,548,892 * | 10/1985 | Iwasaki et al. ................... 430/288.1 |
| 4,548,896 | 10/1985 | Sabongi et al. . |
| 4,555,474 | 11/1985 | Kawamura . |
| 4,557,730 | 12/1985 | Bennett et al. . |
| 4,564,560 | 1/1986 | Tani et al. . |
| 4,565,769 | 1/1986 | Dueber et al. . |
| 4,567,171 | 1/1986 | Mangum . |
| 4,571,377 | 2/1986 | McGinniss et al. . |
| 4,584,260 * | 4/1986 | Iwasaki et al. ................... 430/288.1 |
| 4,595,745 | 6/1986 | Nakano et al. . |
| 4,604,344 | 8/1986 | Irving et al. . |
| 4,605,442 | 8/1986 | Kawashita et al. . |
| 4,613,334 | 9/1986 | Thomas et al. . |
| 4,614,723 | 9/1986 | Schmidt et al. . |
| 4,617,380 | 10/1986 | Hinson et al. . |
| 4,619,998 * | 10/1986 | Burh ................................. 544/193.1 |
| 4,620,875 | 11/1986 | Shimada et al. . |
| 4,620,876 | 11/1986 | Fugii et al. . |
| 4,622,286 | 11/1986 | Sheets . |
| 4,631,085 | 12/1986 | Kawanishi et al. . |
| 4,632,891 | 12/1986 | Banks et al. . |
| 4,632,895 | 12/1986 | Patel et al. . |
| 4,634,644 | 1/1987 | Irving et al. . |
| 4,638,340 | 1/1987 | Iiyama et al. . |
| 4,647,310 | 3/1987 | Shimada et al. . |
| 4,655,783 | 4/1987 | Reinert et al. . |
| 4,663,275 | 5/1987 | West et al. . |
| 4,663,641 | 5/1987 | Iiyama et al. . |
| 4,668,533 | 5/1987 | Miller . |
| 4,672,041 | 6/1987 | Jain . |
| 4,696,888 * | 9/1987 | Buhr ................................. 430/270.1 |
| 4,698,291 | 10/1987 | Koibuchi et al. . |
| 4,701,402 | 10/1987 | Patel et al. . |
| 4,702,996 | 10/1987 | Griffing et al. . |
| 4,704,133 | 11/1987 | Reinert et al. . |
| 4,707,161 | 11/1987 | Thomas et al. . |
| 4,707,425 | 11/1987 | Sasagawa et al. . |
| 4,707,430 | 11/1987 | Ozawa et al. . |
| 4,711,668 | 12/1987 | Shimada et al. . |
| 4,711,802 | 12/1987 | Tannenbaum . |
| 4,713,113 | 12/1987 | Shimada et al. . |
| 4,716,093 * | 12/1987 | Kempf et al. .................... 430/227.1 |
| 4,716,097 * | 12/1987 | Weed ................................ 430/327 |
| 4,720,450 | 1/1988 | Ellis . |
| 4,721,531 | 1/1988 | Wildeman et al. . |
| 4,721,734 | 1/1988 | Gehlhaus et al. . |
| 4,724,021 | 2/1988 | Martin et al. . |
| 4,724,201 | 2/1988 | Okazaki et al. . |
| 4,725,527 | 2/1988 | Robillard . |
| 4,727,824 | 3/1988 | Ducharme et al. . |
| 4,732,615 | 3/1988 | Kawashita et al. . |
| 4,737,190 | 4/1988 | Shimada et al. . |
| 4,737,438 | 4/1988 | Ito et al. . |
| 4,740,451 | 4/1988 | Kohara . |
| 4,745,042 | 5/1988 | Sasago et al. . |
| 4,746,735 | 5/1988 | Kruper, Jr. et al. . |
| 4,752,341 | 6/1988 | Rock . |
| 4,755,450 | 7/1988 | Sanders et al. . |
| 4,761,181 | 8/1988 | Suzuki . |
| 4,766,050 | 8/1988 | Jerry . |
| 4,766,055 | 8/1988 | Kawabata et al. . |
| 4,770,667 | 9/1988 | Evans et al. . |
| 4,772,291 | 9/1988 | Shibanai et al. . |
| 4,772,541 | 9/1988 | Gottschalk . |
| 4,775,386 | 10/1988 | Reinert et al. . |
| 4,786,586 | 11/1988 | Lee et al. . |
| 4,789,382 | 12/1988 | Neumann et al. . |
| 4,790,565 | 12/1988 | Steed . |
| 4,800,149 | 1/1989 | Gottschalk . |
| 4,803,008 | 2/1989 | Ciolino et al. . |
| 4,808,189 | 2/1989 | Oishi et al. . |
| 4,812,139 | 3/1989 | Brodmann . |
| 4,812,517 | 3/1989 | West . |
| 4,813,970 | 3/1989 | Kirjanov et al. . |
| 4,822,714 | 4/1989 | Sanders . |
| 4,831,068 | 5/1989 | Reinert et al. . |
| 4,834,771 | 5/1989 | Yamauchi et al. . |
| 4,837,106 | 6/1989 | Ishikawa et al. . |
| 4,837,331 | 6/1989 | Yamanishi et al. . |
| 4,838,938 | 6/1989 | Tomida et al. . |
| 4,839,269 | 6/1989 | Okazaki et al. . |
| 4,840,869 * | 6/1989 | Kita et al. ......................... 430/191 |
| 4,849,320 | 7/1989 | Irving et al. . |
| 4,853,037 | 8/1989 | Johnson et al. . |
| 4,853,398 | 8/1989 | Carr et al. . |
| 4,854,971 | 8/1989 | Gane et al. . |
| 4,857,438 | 8/1989 | Loerzer et al. . |
| 4,861,916 | 8/1989 | Kohler et al. . |
| 4,865,942 | 9/1989 | Gottschalk et al. . |
| 4,874,391 | 10/1989 | Reinert . |
| 4,874,899 | 10/1989 | Hoelderich et al. . |
| 4,885,395 | 12/1989 | Hoelderich . |
| 4,886,774 | 12/1989 | Doi . |
| 4,892,941 | 1/1990 | Dolphin et al. . |
| 4,895,880 | 1/1990 | Gottschalk . |
| 4,900,581 | 2/1990 | Stuke et al. . |
| 4,902,299 | 2/1990 | Anton . |
| 4,902,725 | 2/1990 | Moore . |
| 4,902,787 | 2/1990 | Freeman . |
| 4,911,732 | 3/1990 | Neumann et al. . |
| 4,911,899 | 3/1990 | Hagiwara et al. . |
| 4,917,956 | 4/1990 | Rohrbach . |
| 4,921,317 | 5/1990 | Suzuki et al. . |
| 4,925,770 | 5/1990 | Ichiura et al. . |
| 4,925,777 | 5/1990 | Inoue et al. . |
| 4,926,190 | 5/1990 | Lavar . |
| 4,933,265 | 6/1990 | Inoue et al. . |
| 4,933,948 | 6/1990 | Herkstroeter . |
| 4,937,161 | 6/1990 | Kita et al. . |
| 4,942,113 | 7/1990 | Trundle . |
| 4,944,988 | 7/1990 | Yasuda et al. . |
| 4,950,304 | 8/1990 | Reinert et al. . |
| 4,952,478 | 8/1990 | Miyagawa et al. . |
| 4,952,680 | 8/1990 | Schmeidl . |
| 4,954,380 | 9/1990 | Kanome et al. . |
| 4,954,416 | 9/1990 | Wright et al. . |
| 4,956,254 | 9/1990 | Washizu et al. . |
| 4,964,871 | 10/1990 | Reinert et al. . |
| 4,965,294 | 10/1990 | Ohngemach et al. . |
| 4,966,607 | 10/1990 | Shinoki et al. . |
| 4,966,828 * | 10/1990 | Doenges et al. .................. 430/281.1 |
| 4,966,833 | 10/1990 | Inoue . |
| 4,968,596 | 11/1990 | Inoue et al. . |

| | | | | | | |
|---|---|---|---|---|---|---|
| 4,968,813 | 11/1990 | Rule et al. . | | 5,166,041 | 11/1992 | Murofushi et al. . |
| 4,985,345 | 1/1991 | Hayakawa et al. . | | 5,169,436 | 12/1992 | Matrick . |
| 4,987,056 | 1/1991 | Imahashi et al. . | | 5,169,438 | 12/1992 | Matrick . |
| 4,988,561 | 1/1991 | Wason . | | 5,173,112 | 12/1992 | Matrick et al. . |
| 4,997,745 | 3/1991 | Kawamura et al. . | | 5,176,984 | 1/1993 | Hipps, Sr. et al. . |
| 5,001,330 | 3/1991 | Koch . | | 5,178,420 | 1/1993 | Shelby . |
| 5,002,853 | 3/1991 | Aoai et al. . | | 5,180,425 | 1/1993 | Matrick et al. . |
| 5,002,993 | 3/1991 | West et al. . | | 5,180,624 | 1/1993 | Kojima et al. . |
| 5,003,142 | 3/1991 | Fuller . | | 5,180,652 | 1/1993 | Yamaguchi et al. . |
| 5,006,758 | 4/1991 | Gellert et al. . | | 5,181,935 | 1/1993 | Reinert et al. . |
| 5,008,302 * | 4/1991 | Husler et al. ............. 522/14 | | 5,185,236 | 2/1993 | Shiba et al. . |
| 5,013,959 | 5/1991 | Kogelschatz . | | 5,187,045 | 2/1993 | Bonham et al. . |
| 5,017,195 | 5/1991 | Satou et al. . | | 5,187,049 | 2/1993 | Sher et al. . |
| 5,023,129 | 6/1991 | Morganti et al. . | | 5,190,565 | 3/1993 | Berenbaum et al. . |
| 5,025,036 | 6/1991 | Carson et al. . | | 5,190,710 | 3/1993 | Kletecka . |
| 5,026,425 | 6/1991 | Hindagolla et al. . | | 5,190,845 | 3/1993 | Hashimoto et al. . |
| 5,026,427 | 6/1991 | Mitchell et al. . | | 5,192,642 * | 3/1993 | Steiner et al. ............. 430/281.1 |
| 5,028,262 | 7/1991 | Barlow, Jr. et al. . | | 5,193,854 | 3/1993 | Borowski, Jr. et al. . |
| 5,028,792 | 7/1991 | Mullis . | | 5,196,295 | 3/1993 | Davis . |
| 5,030,243 | 7/1991 | Reinert . | | 5,197,991 | 3/1993 | Rembold . |
| 5,030,248 | 7/1991 | Meszaros . | | 5,198,330 | 3/1993 | Martic et al. . |
| 5,034,526 | 7/1991 | Bonham et al. . | | 5,202,209 | 4/1993 | Winnik et al. . |
| 5,037,726 | 8/1991 | Kojima et al. . | | 5,202,210 | 4/1993 | Matsuoka et al. . |
| 5,045,435 | 9/1991 | Adams et al. . | | 5,202,211 | 4/1993 | Vercoulen . |
| 5,045,573 | 9/1991 | Kohler et al. . | | 5,202,212 | 4/1993 | Shin et al. . |
| 5,047,556 | 9/1991 | Kohler et al. . | | 5,202,213 | 4/1993 | Nakahara et al. . |
| 5,049,479 * | 9/1991 | Zertani et al. ............. 430/271.1 | | 5,202,215 | 4/1993 | Kanakura et al. . |
| 5,049,777 | 9/1991 | Mechtersheimer . | | 5,202,221 | 4/1993 | Imai et al. . |
| 5,053,320 | 10/1991 | Robbillard . | | 5,205,861 | 4/1993 | Matrick . |
| 5,055,579 | 10/1991 | Pawlowski et al. . | | 5,208,136 | 5/1993 | Zanoni et al. . |
| 5,057,562 | 10/1991 | Reinert . | | 5,209,814 | 5/1993 | Felten et al. . |
| 5,068,140 | 11/1991 | Malhotra et al. . | | 5,219,703 | 6/1993 | Bugner et al. . |
| 5,068,364 | 11/1991 | Takagaki et al. . | | 5,221,334 | 6/1993 | Ma et al. . |
| 5,068,371 * | 11/1991 | Steiner et al. ............. 556/53 | | 5,224,197 | 6/1993 | Zanoni et al. . |
| 5,069,681 | 12/1991 | Bouwknegt et al. . | | 5,224,987 | 7/1993 | Matrick . |
| 5,070,001 | 12/1991 | Stahlhofen . | | 5,226,957 | 7/1993 | Wickramanayake et al. . |
| 5,073,448 | 12/1991 | Vieira et al. . | | 5,227,022 | 7/1993 | Leonhardt et al. . |
| 5,074,885 | 12/1991 | Reinert . | | 5,230,982 | 7/1993 | Davis et al. . |
| 5,075,467 * | 12/1991 | Desobry ............. 556/53 | | 5,241,059 | 8/1993 | Yoshinaga . |
| 5,076,808 | 12/1991 | Hahn et al. . | | 5,244,476 | 9/1993 | Schultz et al. . |
| 5,085,698 | 2/1992 | Ma et al. . | | 5,250,109 | 10/1993 | Chan et al. . |
| 5,087,550 | 2/1992 | Blum et al. . | | 5,254,429 | 10/1993 | Gracia et al. . |
| 5,089,050 | 2/1992 | Vieira et al. . | | 5,256,193 | 10/1993 | Winnik et al. . |
| 5,089,374 | 2/1992 | Saeva . | | 5,258,274 | 11/1993 | Helland et al. . |
| 5,096,456 | 3/1992 | Reinert et al. . | | 5,261,953 | 11/1993 | Vieira et al. . |
| 5,096,489 | 3/1992 | Laver . | | 5,262,276 | 11/1993 | Kawamura . |
| 5,096,781 | 3/1992 | Vieira et al. . | | 5,268,027 | 12/1993 | Chan et al. . |
| 5,098,477 | 3/1992 | Vieira et al. . | | 5,270,078 | 12/1993 | Walker et al. . |
| 5,098,793 | 3/1992 | Rohrbach et al. . | | 5,271,764 | 12/1993 | Winnik et al. . |
| 5,098,806 | 3/1992 | Robillard . | | 5,271,765 | 12/1993 | Ma . |
| 5,106,723 | 4/1992 | West et al. . | | 5,272,201 | 12/1993 | Ma et al. . |
| 5,108,505 | 4/1992 | Moffat . | | 5,275,646 | 1/1994 | Marshall et al. . |
| 5,108,874 | 4/1992 | Griffing et al. . | | 5,279,652 | 1/1994 | Kaufmann et al. . |
| 5,110,706 | 5/1992 | Yumoto et al. . | | 5,282,894 | 2/1994 | Albert et al. . |
| 5,110,709 | 5/1992 | Aoai et al. . | | 5,284,734 | 2/1994 | Blum et al. . |
| 5,114,832 | 5/1992 | Zertani et al. . | | 5,286,286 | 2/1994 | Winnik et al. . |
| 5,124,723 | 6/1992 | Laver . | | 5,286,288 | 2/1994 | Tobias et al. . |
| 5,130,227 | 7/1992 | Wade et al. . | | 5,292,458 * | 3/1994 | Takahashi et al. ............. 264/4.7 |
| 5,133,803 | 7/1992 | Moffatt . | | 5,294,528 | 3/1994 | Furutachi . |
| 5,135,940 | 8/1992 | Belander et al. . | | 5,296,275 | 3/1994 | Goman et al. . |
| 5,139,572 | 8/1992 | Kawashima . | | 5,296,556 | 3/1994 | Frihart . |
| 5,139,687 | 8/1992 | Borgher, Sr. et al. . | | 5,298,030 | 3/1994 | Burdeska et al. . |
| 5,141,556 | 8/1992 | Matrick . | | 5,300,403 | 4/1994 | Angelopolus et al. . |
| 5,141,797 | 8/1992 | Wheeler . | | 5,300,654 | 4/1994 | Nakajima et al. . |
| 5,144,964 | 9/1992 | Demian . | | 5,302,195 | 4/1994 | Helbrecht . |
| 5,147,901 | 9/1992 | Rutsch et al. . | | 5,302,197 | 4/1994 | Wickramanayke et al. . |
| 5,153,104 | 10/1992 | Rossman et al. . | | 5,306,600 * | 4/1994 | Steiner et al. ............. 430/281.1 |
| 5,153,105 | 10/1992 | Sher et al. . | | 5,310,778 | 5/1994 | Shor et al. . |
| 5,153,166 | 10/1992 | Jain et al. . | | 5,312,713 | 5/1994 | Yokoyama et al. . |
| 5,160,346 | 11/1992 | Fuso et al. . | | 5,312,721 | 5/1994 | Gesign . |
| 5,160,372 | 11/1992 | Matrick . | | 5,324,349 | 6/1994 | Sano et al. . |

| | | |
|---|---|---|
| 5,328,504 | 7/1994 | Ohnishi . |
| 5,330,860 | 7/1994 | Grot et al. . |
| 5,334,455 | 8/1994 | Noren et al. . |
| 5,338,319 | 8/1994 | Kaschig et al. . |
| 5,340,631 | 8/1994 | Matsuzawa et al. . |
| 5,340,854 | 8/1994 | Martic et al. . |
| 5,344,483 | 9/1994 | Hinton . |
| 5,356,464 | 10/1994 | Hickman et al. . |
| 5,362,592 | 11/1994 | Murofushi et al. . |
| 5,368,689 | 11/1994 | Agnemo . |
| 5,372,387 | 12/1994 | Wajda . |
| 5,372,917 | 12/1994 | Tsuchida et al. . |
| 5,374,335 | 12/1994 | Lindgren et al. . |
| 5,376,503 | 12/1994 | Audett et al. . |
| 5,383,961 | 1/1995 | Bauer et al. . |
| 5,384,186 | 1/1995 | Trinh . |
| 5,393,580 | 2/1995 | Ma et al. . |
| 5,401,303 | 3/1995 | Stoffel et al. . |
| 5,401,562 | 3/1995 | Akao . |
| 5,415,686 | 5/1995 | Kurabayashi et al. . |
| 5,415,976 | 5/1995 | Ali . |
| 5,424,407 | 6/1995 | Tanaka et al. . |
| 5,425,978 | 6/1995 | Berneth et al. . |
| 5,426,164 | 6/1995 | Babb et al. . |
| 5,427,415 | 6/1995 | Chang . |
| 5,429,628 | 7/1995 | Trinh et al. . |
| 5,431,720 | 7/1995 | Nagai et al. . |
| 5,432,274 | 7/1995 | Luong et al. . |
| 5,445,651 | 8/1995 | Thoen et al. . |
| 5,445,842 | 8/1995 | Tanaka et al. . |
| 5,455,074 | 10/1995 | Nohr et al. . |
| 5,455,143 | 10/1995 | Ali . |
| 5,459,014 | 10/1995 | Nishijima et al. . |
| 5,464,472 | 11/1995 | Horn et al. . |
| 5,466,283 | 11/1995 | Kondo et al. . |
| 5,474,691 | 12/1995 | Severns . |
| 5,475,080 | 12/1995 | Gruber et al. . |
| 5,476,540 | 12/1995 | Shields et al. . |
| 5,479,949 | 1/1996 | Battard et al. . |
| 5,489,503 | 2/1996 | Toan . |
| 5,498,345 | 3/1996 | Jollenbeck et al. . |
| 5,501,774 | 3/1996 | Burke . |
| 5,501,902 | 3/1996 | Kronzer . |
| 5,503,664 | 4/1996 | Sano et al. . |
| 5,509,957 | 4/1996 | Toan et al. . |
| 5,510,224 * | 4/1996 | Takahashi et al. .................. 430/130 |
| 5,531,821 | 7/1996 | Wu . |
| 5,532,112 | 7/1996 | Kohler et al. . |
| 5,541,633 | 7/1996 | Winnik et al. . |
| 5,543,459 | 8/1996 | Hartmann et al. . |
| 5,545,676 * | 8/1996 | Palazzotto et al. ................... 522/15 |
| 5,569,529 | 10/1996 | Becker et al. . |
| 5,571,313 | 11/1996 | Mafune et al. . |
| 5,575,891 | 11/1996 | Trokhan et al. . |
| 5,580,369 | 12/1996 | Belding et al. . |
| 5,591,489 | 1/1997 | Dragner et al. . |
| 5,597,405 | 1/1997 | Grigoryan et al. . |
| 5,607,803 | 3/1997 | Murofushi et al. . |
| 5,616,443 | 4/1997 | Nohr et al. . |
| 5,635,297 | 6/1997 | Ogawa et al. . |
| 5,643,356 | 7/1997 | Nohr et al. . |
| 5,643,631 | 7/1997 | Donigian et al. . |
| 5,643,701 | 7/1997 | Nohr et al. . |
| 5,645,964 | 7/1997 | Nohr et al. . |
| 5,672,392 | 9/1997 | De Clercq et al. . |
| 5,681,380 | 10/1997 | Nohr et al. . |
| 5,683,843 | 11/1997 | Nohr et al. . |
| 5,685,754 | 11/1997 | Nohr et al. . |
| 5,686,503 | 11/1997 | Nohr et al. . |
| 5,700,582 | 12/1997 | Sargeant et al. . |
| 5,700,850 | 12/1997 | Nohr et al. . |
| 5,705,247 | 1/1998 | Arai et al. . |
| 5,709,955 | 1/1998 | Nohr et al. . |
| 5,709,976 | 1/1998 | Malhotra . |
| 5,721,287 | 2/1998 | Nohr et al. . |
| 5,733,693 | 3/1998 | Nohr et al. . |
| 5,738,932 | 4/1998 | Kondo et al. . |
| 5,739,175 | 4/1998 | Nohr et al. . |
| 5,747,550 | 5/1998 | Nohr et al. . |
| 5,773,182 | 6/1998 | Nohr et al. . |
| 5,782,963 | 7/1998 | Nohr et al. . |
| 5,786,132 | 7/1998 | Nohr et al. . |
| 5,798,015 | 8/1998 | Nohr et al. . |
| 5,811,199 | 9/1998 | MacDonald et al. . |
| 5,837,429 | 11/1998 | Nohr et al. . |
| 5,849,411 | 12/1998 | Nohr et al. . |
| 5,855,655 | 1/1999 | Nohr et al. . |
| 5,865,471 | 2/1999 | Nohr et al. . |
| 5,883,161 | 3/1999 | Wood et al. . |
| 5,885,337 | 3/1999 | Nohr et al. . |
| 5,891,229 | 4/1999 | Nohr et al. . |
| 5,911,855 | 6/1999 | Dransmann et al. . |
| 5,939,238 * | 8/1999 | Barr et al. ......................... 430/281.1 |
| 6,017,660 * | 1/2000 | Palazzotto et al. ..................... 430/17 |
| 6,060,215 * | 5/2000 | Amanolura et al. .............. 430/281.1 |

FOREIGN PATENT DOCUMENTS

| | | |
|---|---|---|
| 413257 | 10/1932 | (CA) . |
| 458808 | 12/1936 | (CA) . |
| 460268 | 10/1949 | (CA) . |
| 461082 | 11/1949 | (CA) . |
| 463021 | 2/1950 | (CA) . |
| 463022 | 2/1950 | (CA) . |
| 465495 | 5/1950 | (CA) . |
| 465496 | 5/1950 | (CA) . |
| 465499 | 5/1950 | (CA) . |
| 483214 | 5/1952 | (CA) . |
| 517364 | 10/1955 | (CA) . |
| 537687 | 3/1957 | (CA) . |
| 552565 | 2/1958 | (CA) . |
| 571792 | 3/1959 | (CA) . |
| 779239 | 2/1968 | (CA) . |
| 930103 | 7/1973 | (CA) . |
| 2053094 | 4/1992 | (CA) . |
| 603767 | 8/1978 | (CH) . |
| 197808 | 5/1988 | (CH) . |
| 94118 | 5/1958 | (CS) . |
| 1047787 | 12/1957 | (DE) . |
| 1022801 | 1/1958 | (DE) . |
| 1039835 | 9/1958 | (DE) . |
| 1040562 | 10/1958 | (DE) . |
| 1045414 | 12/1958 | (DE) . |
| 1047013 | 12/1958 | (DE) . |
| 1132540 | 7/1962 | (DE) . |
| 1154069 | 9/1963 | (DE) . |
| 1240811 | 5/1967 | (DE) . |
| 2202497 | 8/1972 | (DE) . |
| 2432563 | 2/1975 | (DE) . |
| 2437380 | 2/1975 | (DE) . |
| 2444520 | 3/1975 | (DE) . |
| 2416259 | 10/1975 | (DE) . |
| 2714978 | 10/1977 | (DE) . |
| 2722264 | 11/1978 | (DE) . |
| 158237 | 1/1983 | (DE) . |
| 3126433 | 1/1983 | (DE) . |
| 3415033 | 10/1984 | (DE) . |
| 271512 | 9/1989 | (DE) . |
| 3921600 | 1/1990 | (DE) . |
| 3833437 | 4/1990 | (DE) . |
| 3833438 | 4/1990 | (DE) . |
| 004036328 | 7/1991 | (DE) . |
| 4132288 | 4/1992 | (DE) . |

| | | | | | | |
|---|---|---|---|---|---|---|
| 4126461 | 2/1993 | (DE) . | | 58-125770 | 7/1983 | (JP) . |
| 0003884 | 9/1979 | (EP) . | | 58-222164 | 12/1983 | (JP) . |
| 0029284 | 5/1981 | (EP) . | | 59-89360 | 5/1984 | (JP) . |
| 0127574 | 12/1984 | (EP) . | | 29219270 | 12/1984 | (JP) . |
| 0 209 831 | 1/1987 | (EP) . | | 59-219270 | 4/1985 | (JP) . |
| 0223587 | 5/1987 | (EP) . | | 60-192729 | 10/1985 | (JP) . |
| 0262533 | 4/1988 | (EP) . | | 60-239739 | 11/1985 | (JP) . |
| 0280458 | 8/1988 | (EP) . | | 60-239740 | 11/1985 | (JP) . |
| 0 303 803 | 2/1989 | (EP) . | | 60-239741 | 11/1985 | (JP) . |
| 0308274 | 3/1989 | (EP) . | | 60-239743 | 11/1985 | (JP) . |
| 0351615 | 1/1990 | (EP) . | | 61-14994 | 1/1986 | (JP) . |
| 0371304 | 6/1990 | (EP) . | | 61-14995 | 1/1986 | (JP) . |
| 0373662 | 6/1990 | (EP) . | | 61-21184 | 1/1986 | (JP) . |
| 0375160 | 6/1990 | (EP) . | | 61-288 | 1/1986 | (JP) . |
| 0390439 | 10/1990 | (EP) . | | 613781 | 1/1986 | (JP) . |
| 0458140A1 | 10/1991 | (EP) . | | 61-25885 | 2/1986 | (JP) . |
| 0458140 | 11/1991 | (EP) . | | 61-30592 | 2/1986 | (JP) . |
| 0468465 | 1/1992 | (EP) . | | 61-40366 | 2/1986 | (JP) . |
| 0 469 595 | 2/1992 | (EP) . | | 61-77846 | 4/1986 | (JP) . |
| 0 475 075 | 3/1992 | (EP) . | | 61-128973 | 6/1986 | (JP) . |
| 0542286 | 5/1993 | (EP) . | | 61-97025 | 9/1986 | (JP) . |
| 000571190 | 11/1993 | (EP) . | | 61-222789 | 10/1986 | (JP) . |
| 0 605 840 | 7/1994 | (EP) . | | 61-247703 | 11/1986 | (JP) . |
| 0608433 | 8/1994 | (EP) . | | 61-285403 | 12/1986 | (JP) . |
| 0609159 | 8/1994 | (EP) . | | 627703 | 1/1987 | (JP) . |
| 0 635 380 | 1/1995 | (EP) . | | 62-100557 | 5/1987 | (JP) . |
| 0639664 | 2/1995 | (EP) . | | 62-97881 | 5/1987 | (JP) . |
| 0 673 779 | 9/1995 | (EP) . | | 62-127281 | 6/1987 | (JP) . |
| 0 716 929 | 6/1996 | (EP) . | | 424756 | 1/1988 | (JP) . |
| 0 737 592 | 10/1996 | (EP) . | | 63-43959 | 2/1988 | (JP) . |
| 0755984 | 1/1997 | (EP) . | | 63-48370 | 3/1988 | (JP) . |
| 0 805 152 | 11/1997 | (EP) . | | 63-95439 | 4/1988 | (JP) . |
| 0 861 880 | 9/1998 | (EP) . | | 63-95440 | 4/1988 | (JP) . |
| 2245010 | 4/1975 | (FR) . | | 63-95445 | 4/1988 | (JP) . |
| 2383157 | 10/1978 | (FR) . | | 63-95446 | 4/1988 | (JP) . |
| 275245 | 10/1928 | (GB) . | | 63-95447 | 4/1988 | (JP) . |
| 349339 | 5/1931 | (GB) . | | 63-95448 | 4/1988 | (JP) . |
| 355686 | 8/1931 | (GB) . | | 63-95449 | 4/1988 | (JP) . |
| 399753 | 10/1933 | (GB) . | | 63-95450 | 4/1988 | (JP) . |
| 441085 | 1/1936 | (GB) . | | 63-151946 | 6/1988 | (JP) . |
| 463515 | 4/1937 | (GB) . | | 63-164953 | 7/1988 | (JP) . |
| 492711 | 9/1938 | (GB) . | | 63-165498 | 7/1988 | (JP) . |
| 518612 | 3/1940 | (GB) . | | 63-223077 | 9/1988 | (JP) . |
| 539912 | 9/1941 | (GB) . | | 63-223078 | 9/1988 | (JP) . |
| 626727 | 7/1947 | (GB) . | | 63-243101 | 10/1988 | (JP) . |
| 600451 | 4/1948 | (GB) . | | 63-199781 | 12/1988 | (JP) . |
| 616362 | 1/1949 | (GB) . | | 64-15049 | 1/1989 | (JP) . |
| 618616 | 2/1949 | (GB) . | | 6429337 | 1/1989 | (JP) . |
| 779389 | 7/1957 | (GB) . | | 64-40948 | 2/1989 | (JP) . |
| 1150987 | 5/1969 | (GB) . | | 89014948 | 3/1989 | (JP) . |
| 1372884 | 11/1974 | (GB) . | | 1-128063 | 5/1989 | (JP) . |
| 2146357 | 4/1985 | (GB) . | | 1146974 | 6/1989 | (JP) . |
| 662500 | 4/1964 | (IT) . | | 01210477 | 8/1989 | (JP) . |
| 43-15663 | 7/1968 | (JP) . | | 1288854 | 11/1989 | (JP) . |
| 47-26653 | 7/1972 | (JP) . | | 2-58573 | 2/1990 | (JP) . |
| 47-45409 | 11/1972 | (JP) . | | 292957 | 4/1990 | (JP) . |
| 49-8909 | 2/1974 | (JP) . | | 2179642 | 7/1990 | (JP) . |
| 50-65592 | 6/1975 | (JP) . | | 2282261 | 11/1990 | (JP) . |
| 51-17802 | 2/1976 | (JP) . | | 3-134072 | 6/1991 | (JP) . |
| 53-104321 | 9/1978 | (JP) . | | 03163566 | 7/1991 | (JP) . |
| 55-62059 | 5/1980 | (JP) . | | 3-170415 | 7/1991 | (JP) . |
| 55-90506 | 7/1980 | (JP) . | | 3-206439 | 9/1991 | (JP) . |
| 56-8134 | 1/1981 | (JP) . | | 3-258867 | 11/1991 | (JP) . |
| 0014233 | 2/1981 | (JP) . | | 3-203694 | 12/1991 | (JP) . |
| 56-14569 | 2/1981 | (JP) . | | 3284668 | 12/1991 | (JP) . |
| 56-24472 | 3/1981 | (JP) . | | 4023884 | 1/1992 | (JP) . |
| 56-36556 | 4/1981 | (JP) . | | 4023885 | 1/1992 | (JP) . |
| 57-61055 | 4/1982 | (JP) . | | 4-45174 | 2/1992 | (JP) . |
| 57-128283 | 8/1982 | (JP) . | | 4100801 | 4/1992 | (JP) . |
| 57-171775 | 10/1982 | (JP) . | | 4-136075 | 5/1992 | (JP) . |
| 58-124452 | 7/1983 | (JP) . | | 04356087 | 12/1992 | (JP) . |

| | | |
|---|---|---|
| 543806 | 2/1993 | (JP) . |
| 561220 | 3/1993 | (JP) . |
| 5080506 | 4/1993 | (JP) . |
| 05119506 | 5/1993 | (JP) . |
| 5134447 | 5/1993 | (JP) . |
| 5-140498 | 6/1993 | (JP) . |
| 2-219869 | 9/1993 | (JP) . |
| 5263067 | 10/1993 | (JP) . |
| 680915 | 3/1994 | (JP) . |
| 6116555 | 4/1994 | (JP) . |
| 6116556 | 4/1994 | (JP) . |
| 6116557 | 4/1994 | (JP) . |
| 6-175584 | 6/1994 | (JP) . |
| 6214339 | 8/1994 | (JP) . |
| 6256494 | 9/1994 | (JP) . |
| 6256633 | 9/1994 | (JP) . |
| 7113828 | 4/1972 | (NL) . |
| 1310767 | 5/1987 | (RU) . |
| 1772118 | 10/1992 | (RU) . |
| 92/11295 | 7/1992 | (WO) . |
| 93/06597 | 4/1993 | (WO) . |
| 94/01503 | 1/1994 | (WO) . |
| 94/22500 | 10/1994 | (WO) . |
| 94/22501 | 10/1994 | (WO) . |
| 95/04955 | 2/1995 | (WO) . |
| 95/28285 | 10/1995 | (WO) . |
| 96/00740 | 1/1996 | (WO) . |
| 96/19502 | 6/1996 | (WO) . |
| 96/22335 | 7/1996 | (WO) . |
| 96/24636 | 8/1996 | (WO) . |
| 97/20000 | 6/1997 | (WO) . |
| 97/35933 | 10/1997 | (WO) . |
| 98/23695 | 6/1998 | (WO) . |

OTHER PUBLICATIONS

Maki, Y. et al. "A novel heterocyclic N–oxide, pyrimido[5,4–g]pteridinetetrone 5–oxide, with multifunctional photo-oxidative properties" Chemical Abstracts 122 925 [No. 122:31350 F] 1995.

Abstract of patent, JP 6–80915 (Canon Inc.), Mar. 22, 1994.

Abstract of patent, JP 06–43573 (Iku Meji) (Feb. 18, 1994).

Pitchumani, K. et al. "Modification of chemical reactivity upon cyclodextrin encapsulation" Chemical Abstracts 121 982 [No. 121:13362 4v] 1994.

Wijesekera, T.P., et al. Synthetic Aspects of Pophyrin and Metalloporphyrin Chemistry Metalloporpyrins in Catalytic Oxidations pp. 202–203, 206–207, 1994.

Derwent Publications Ltd., London, JP 05297627 (Fujitsu Ltd.), Nov. 12, 1993. (Abstract).

Patent Abstracts of Japan, JP 5241369 (Bando Chem Ind Ltd et al.), Sep. 21, 1993. (Abstract).

Derwent Publications Ltd., London, JP 05232738 (Yamazaki, T.), Sep. 10, 1993. (Abstract).

Derwent Publications Ltd., London, EP 000559310 (Zeneca Ltd.), Sep. 8, 1993. (Abstract).

Derwent Publications Ltd., London, J,A, 5–230410 (Seiko Epson Corp), Sep. 7, 1993. (Abstract).

Derwent Publications Ltd., London, JP 5–230407 (Mitsubishi Kasei Corp), Sep. 7, 1993, (Abstract).

Abstract Of Patent, JP 405230410 ( Seiko Epson Corp.), Sep. 7, 1993. (Abstract).

Abstract Of Patent, JP 405230407 ( Mitsubishi Kasei Corp.), Sep. 7, 1993. (Abstract).

Patent Abstracts of Japan, JP 5197198 (Bando Chem Ind Ltd et al.), Aug. 6, 1993. (Abstract).

Database WPI—Derwent Publications Ltd., London, J,A, 5197069 (Bando Chem), Aug. 6, 1993. (Abstract).

Abstract of patent, JP 5–195450 (Nitto Boseki Co. Ltd), Aug. 3, 1993.

Derwent World Patents Index JP 5186725 (Seiko Epson Corp.), Jul. 27, 1993. abstract.

Patent Abstracts of Japan, JP 5181308 (Bando Chem Ind Ltd et al.), Jul. 23, 1992. (Abstract).

Patent Abstracts of Japan, JP 5181310 (Bando Chem Ind Ltd et al.), Jul. 23, 1993. (Abstract).

Derwent Publications Ltd., London, JP 5–132638 (Mitsubishi Kasei Corp), May 28, 1993. (Abstract).

Abstract Of Patent, JP 405132638 ( Mitsubishi Kasei Corp.), May 28, 1993. (Abstract).

Derwent Publications Ltd., London, JP 5–125318 (Mitsubishi Kasei Corp), May 21, 1993. (Abstract).

Abstract Of Patent, JP 405125318 ( Mitsubishi Kasei Corp.), May 21, 1993. (Abstract).

Abstract of patent, JP 05–117200 (Hidefumi Hirai et al.) (May 14, 1993).

Derwent World Patents Index, JP 5117105 (Mitsui Toatsu Chem Inc.) May 14, 1993.

Derwent Publications Ltd., London, JP 05061246 (Ricoh KK), Mar. 12, 1993. (Abstract).

Husain, N. et al. "Cyclodextrins as mobile–phase additives in reversed–phase HPLC" American Laboratory 82 80–87 1993.

Hamilton, D.P. "Tired of Shredding? New Ricoh Method Tries Different Tack" Wall Street Journal B2 1993.

"Cyclodextrins: A Breakthrough for Molecular Encapsulation" American Maize Products Co. (AMAIZO) 1993.

Duxbury "The Photochemistry and Photophysics of Triphenylmethane Dyes in Solid Liquid Media" Chemical Review 93 381–433 1993.

Abstract of patent, JP 04–351603 (Dec. 7, 1992).

Abstract of patent, JP 04–351602 1992.

Derwent Publications Ltd., London, JP 404314769 (Citizen Watch Co. Ltd.), Nov. 5, 1992. (Abstract).

Abstract of patent, JP 04315739 1992.

Derwent Publications Ltd., London, JP 04300395 (Funai Denki KK), Oct. 23, 1992. (Abstract).

Derwent Publications Ltd., London, JP 404213374 (Mitsubishi Kasei Corp), Aug. 4, 1992. (Abstract).

Abstract of patent, JP 04–210228 1992.

Abstract Of Patent, JP 404202571 (Canon Inc.), Jul. 23, 1992. (Abstract).

Abstract Of Patent, JP 404202271 (Mitsubishi Kasei Corp.), Jul. 23, 1992. (Abstract).

Derwent WPI, JP 4–197657 (Toshiba KK) Jul. 17, 1992, abstract.

Derwent Publications Ltd., London, JP 4–189877 (Seiko Epson Corp), Jul. 8, 1992. (Abstract).

Derwent Publications Ltd., London, JP 404189876 (Seiko Epson Corp), Jul. 8, 1992. (Abstract).

Abstract Of Patent, JP 404189877 (Seiko Epson Corp.), Jul. 8, 1992. (Abstract).

Derwent Publications Ltd., London, J,A, 4–170479 (Seiko Epson Corp), Jun. 18, 1992. (Abstract).

Abstract of patent, JP 04–81402 1992.

Abstract of patent, JP 04–81401 1992.

Kogelschatz "Silent–discharge driven excimer UV sources and their applications" Applied Surface Science 410–423 1992.

Derwent Publications, Ltd., London, JP 403269167 (Japan Wool Textile KK), Nov. 29, 1991 (Abstract).

Derwent Publications Ltd., London, JO 3247676 (Canon KK), Nov. 5, 1991 (Abstract).
Abstract of patent, JP 03–220384 1991.
Patent Abstracts of Japan, JP 03184896 (Dainippon Printing Co Ltd.) Aug. 12, 1991.
Derwent Publications Ltd., London, JP 3167270 (Mitsubishi Kasei Corp), Jul. 19, 1991. (Abstract).
Derwent Publications Ltd., London, JO 3167270 (Mitsubishi Kasei Corp.), Jul. 19, 1991 (Abstract).
Derwent World Patents Index EP 435536 (Canon KK) Jul. 3, 1991. abstract.
Derwent Publications Ltd., London, JO 3093870 (Dainippon Ink Chem KK.), Apr. 18, 1991 (Abstract).
Abstract of patent, JP 06369890 1991.
Kogelschatz, U. et al. "New Excimer UV Sources for Industrial Applications" *ABB Review* 391 1–10 1991.
Abstract of patent, JP 03–41165 1991.
"Coloring/Decoloring Agent for Tonor Use Developed" *Japan Chemical Week* 1991.
Braithwaite, M., et al. "Formulation" *Chemistry & Technology of UV & EB Formulation for Coatings, Inks & Paints*. IV 11–12 1991.
*Scientific Polymer Products, Inc. Brochure* 24–31 1991.
Dietliker, K. "Photoiniators for Free Radical and Catioinc Polymerisation" *Chem & Tech of UV & EB Formulation for Coatings, Inks & Paints* III 61, 63, 229–232, 280, 405, 1991.
Esrom et al. "Large area Photochemical Dry Etching of Polymers iwth Incoherent Excimer UV Radiation" *MRS Materials Research Society* 1–7 1991.
Esrom et al. Excimer Laser–Induced Decomposition of Aluminum Nitride *Materials Research Society Fall Meeting* 1–6 1991.
Esrom et al "Metal deposition with a windowless VUV excimer source" *Applied Surface Science* 1–5 1991.
Esrom "Excimer Laser–Induced Surface Activation of Aln for Electroless Metal Deposition" *Mat. Res. Sco.1Symp. Proc.* 204 457–465 1991.
Zhang et al. "UV–induced decompositin of adsorbed Cu–acetylacetonate films at room temperature for electroless metal plating" *Applied Surface Science* 1–6 1991.
"Coloring/Decoloring Agent for Tonor Use Developed" *Japan Chemical Week* 1991.
"German company develops reuseable paper" *Pulp & Paper* 1991.
Abstract of patent, JP 02289652 1990.
Ohashi et al. "Molecular Mechanics Studies on Inclusion Compounds of Cyanine Dye Monomers and Dimers in Cyclodextrin Cavities," *J. Am. Chem. Soc.* 112 5824–5830 1990.
Kogelschatz et al. "New Incoherent Ultraviolet Excimer Sources for Photolytic Material Deposition," *Laser Und Optoelektronik* 1990.
Patent Abstracts of Japan, JP 02141287 (Dainippon Printing Co Ltd.) May 30, 1990.
Abstract of Patent, JP 0297957, (Fuji Xerox Co., Ltd.) 1990.
Derwent Publications Ltd., London, JP 2091166 (Canon KK), Mar. 30, 1990. (Abstract).
Esrom et al. "Metal Deposition with Incoherent Excimer Radiation" *Mat. Res. Soc. Symp. Proc.* 158 189–198 1990.
Esrom "UV Excimer Laser–Induced Deposition of Palladium from palladiym Acetate Films" *Mat. Res. Soc. Symp. Proc.* 158 109–117 1990.

Kogelschatz, U. "Silent Discharges for the Generation of ultraviolet and vacuum ultraviolet excimer radiation" *Pure & Applied Chem.* 62 1667–74 1990.
Esrom et al. "Investigation of the mechanism of the UV–induced palladium depostions processf from thin solid palladium acetate filsm" *Applied Surface Science* 46 158–162 1990.
Zhang et al. "VUV synchrotron radiation processing of thin palladium acetate spin–on films for metallic surface patterning" *Applied Surface Science* 46 153–157 1990.
Brennan et al. "Stereoelectronic effects in ring closure reactions: the 2'–hydroxychalcone—flavanone equilibrium, and related systems," *Canadian J. Chem.* 68 (10) pp. 1780–1785 1990.
Abstract of patent, JP 01–299083 1989.
Derwent Publications Ltd., London, J,0, 1182379 (Canon KK), Jul. 20, 1989. (Abstract).
Derwent Publications Ltd., London, JO 1011171 (Mitsubishi Chem Ind. KK.), Jan. 13, 1989 (Abstract).
Gruber, R.J., et al. "Xerographic Materials" *Encyclopedia of Polymer Science and Engineering* 17 918–943 1989.
Pappas, S.P. "Photocrosslinking" *Comph. Pol. Sci.* 6 135–148 1989.
Pappas, S.P. "Photoinitiated Polymerization" *Comph. Pol. Sci.* 4 337–355 1989.
Kirilenko, G.V. et al. "An analog of the vesicular process with amplitude modulation of the incident light beam" *Chemical Abstracts* 111 569 [No. 111:12363 3b] 1989.
Esrom et al. "UV excimer laser–induced pre–nucleation of surfaces followed by electroless metallization" *Chemtronics* 4 216–223 1989.
Esrom et al. "VUV light–induced depostion of palladium using an incoherent Xe2* excimer source" *Chemtronics* 4 1989.
Esrom et al. "UV Light–Induced Deposition of Copper Films" C5–719–C5–725 1989.
Falbe et al. *Rompp Chemie Lexikon* 9 270 1989.
Allen, Norman S. *Photopolymerisation and Photoimaging Science and Technology* pp. 188–199; 210–239 1989.
Patent Abstracts of Japan, JP 63297477 (Fuji Photo Film Co. Ltd.) Dec. 5, 1988, abstract.
Derwent Publications, Ltd., London, SU 1423656 (Kherson Ind Inst), Sep. 15, 1988 (Abstract).
Derwent Publications, Ltd., London, EP 0280653 (Ciba GeigyAG), Aug. 31, 1988 (Abstract).
Abstract of patent, JP 63–190815 1988.
Patent Abstracts of Japan, JP 63179985 (Tomoegawa Paper Co. Ltd.), Jul. 23, 1988.
Derwent World Patents Index, JP 63179977 (Tomoegawa Paper Mfg Co Ltd), Jul. 23, 1988.
Furcone, S.Y. et al. "Spin–on B14Sr3Ca3Cu4O16+x superconducting thin films from citrate precursors," *Appl. Phys. Lett.* 52(2 5) 2180–2182 1988.
Abstract of patent, JP 63–144329 1988.
Abstract of patent, JP 63–130164 1988.
Derwent Publications, Ltd., London, J6 3112770 (Toray Ind Inc), May 17, 1988 (Abstract).
Derwent Publications, Ltd., London, J6 3108074 (Konishiroku Photo KK), May 12, 1988 (Abstract).
Derwent Publications, Ltd., London,J6 3108073 (Konishiroku Photo KK), May 12, 1988 (Abstract).
Abstract of patent, JP 61–77846 1988.
Abstract of patent, JP 63–73241 1988.
Abstract of patent, JP 63–47762, 1988

Abstract of patent, JP 63–47763, 1988.
Abstrat of patent, JP 63–47764, 1988.
Abstract of patent, JP 6347765 1988.
Eliasson, B., et al. "UV Excimer Radiation from Dielectric–Barrier Discharges" *Applied Physics B* 46 299–303 1988.
Eliasson et al. "New Trends in High Intensity UV Generation" *EPA Newsletter* (32) 29–40 1988.
Cotton, F.A. "Oxygen: Group Via(16)" *Advanced Inorganic Chemistry* 5th ed. 473–474 1988.
Derwent Publications, Ltd., London, J6 2270665 (Konishiroku Photo KK), Nov. 25, 1987 (Abstract).
Abstract of patent, JP 62–215261 1987.
Derwent World Patents Index JP 62064874 (Dainichiseika Color & Chem Mfg.), Mar. 23, 1987. abstract.
Database WPI, Derwent Publications Ltd., London, JP 62032082 (Mitsubishi Denki KK), Feb. 12, 1987. (Abstract).
Abstract of patent, JP 62–32082 1987.
Derwent Publications Ltd., London, J6 2007772 (Alps Elecric KK.), Jan. 14, 1987 (Abstract).
Gross et al. "Laser direct–write metallization in thin palladium acetate films" *J. App. Phys.* 61 (4) 1628–1632 1987.
Al–Ismail et al. "Some experimental results on thin polypropylene films loaded with finely–dispersed copper" *Journal of Materials Science* 415–418 1987.
Baufay et al. "Optical self–regulation during laser–induced oxidation of copper" *J. Appl. Phys* 61 (9) 4640–4651 1987.
Al–Ismail et al. "Some experimental results on thin polypropylene films loaded with finely–dispersed copper" *Journal of Materials Science* 415–418 1987.
Derwent Publications Ltd., London, JA 0284478 (Sanyo Chem Ind Ltd.), Dec. 15, 1986 (Abstract).
Abstract of patent, JP 61251842 1986.
Database WPI, Derwent Publications Ltd., London, GB; SU, A, 1098210 (Kutulya L A) Jun. 23, 1986.
Abstract of patent, JP 61–97025 1986.
Abstract of patent, JP 61–87760 1986.
Derwent Publications Ltd., London, DL 0234731 (Karl Marx Univ. Leipzig), Apr. 9, 1986. (Abstract).
Derwent World Patents Index, SU 1219612 (AS USSR NON–AQ SOLN) Mar. 23, 1986.
Derwent Publications, Ltd., London, J6 1041381 (Osaka Prefecture), Feb. 27, 1986 (Abstract).
Dialog, JAPIO, JP 61–034057 (Ciba Geigy AG) Feb. 18, 1986.
Derwent World Patents Index, JP 61027288 (sumitomo Chem Ind KK) Feb. 6, 1986.
Sakai et al. "A Novel and Practical Synthetic Method of 3(2H)–Furanone Derivatives," *J. Heterocyclie Chem.* 23 pp. 1199–1201 1986.
Jellinek, H.H.G. et al. "Evolution of H20 and CO2 During the Copper–Catalyzed Oxidation of Isotactic Polypropylene," *J. Polymer Sci.* 24 389–403 1986.
Jellinek, H.H.G. et al. "Diffusion of Ca2+ Catalysts from Cu–Metal Polymer or Cu–Oxide/Polymer Interfaces into Isotactic Polypropylene," *J. Polymer Sci.* 24 503–510 1986.
John J. Eisch and Ramiro Sanchez "Selective, Oxophilic Imination of Ketones with Bis (dichloroaluminum) Phenylimide" *J. Org. Chem.* 51 (10) 1848–1852 1986.
Derwent Publications Ltd., London, J6 0226575 (Sumitomo Chem Ind Ltd.), Oct. 11, 1985 (Abstract).
Abstract of patent, JP 60–156761 1985.

Derwent World Patents Index DE 3443565 (Mitsubishi Yuka Fine Che. et al.) Jul. 11, 1985. abstract.
Derwent Publications Ltd., London, J,A, 0011451 (Fugi Photo Film KK), Jan. 21, 1985. (Abstract).
Derwent Publications, Ltd., London J6 0011449 –A (Taoka Chemical KK) Jan. 21, 1985 (abstract).
Derwent World Patents Index JP 60–008088 (Mitsubishi Paper Mills Ltd.) Jan. 16, 1985. abstract.
Roos, G. et al. "Textile applications of photocrosslinkable polymers" *Chemical Abstracts* 103 57 [No. 103:23690j ] 1985.
Beck, M.T., et al. Mechanism of the autophotosensitized formulation of porphyrins in the reaction of pyrrole and m–disulfonated *Chemical Abstracts* 198 5:45 362 1985.
Derwent World Patents Index, EP 127574 (Ciba Geigy AG), Dec. 5, 1984.
Derwent Publications Ltd., London, JP 0198187 (Canon KK), Nov. 9, 1984. (Abstract).
Derwent Publications Ltd., London, J,A, 0169883 (Ricoh KK), Sep. 25, 1984. (Abstract).
Derwent Publications Ltd., London, JA 0169883 (Ricoh KK), Sep. 25, 1984 (Abstract).
Derwent Publications Ltd., London, JA 0198187 (Canon KK), Nov. 9, 1984 (Abstract).
Derwent Publications Ltd., London, J,A, 0053563 (Dainippon Toryo KK), Mar. 28, 1984. (Abstract).
Derwent Publications Ltd., London, J,A, 0053562 (Dainippon Toryo KK), Mar. 28, 1984. (Abstract).
Abstract of Patent, JA 0053563 (Dainippon Toryo KK), Mar. 28, 1984 (Abstract).
Abstract of Patent, JA 0053562 (Dainippon Toryo KK), Mar. 28, 1984 (Abstract).
Derwent Publications Ltd., London, J,A, 0051961 (Dainippon Toryo KK), Mar. 26, 1984. (Abstract).
Abstract of Patent, JA 0051961 (Dainippon Toryo KK), Mar. 26, 1984 (Abstract).
Saenger, W. "Structural Aspects of Cyclodextrins and Their Inclusion Complexes" *Inclusion Compounds—Structural Aspects of Inclusion Compounds formed by Organic Host* 2 231–259 1984.
Szejtli "Industrial Applications of Cyclodextrins" *Inclusion Compounds: Physical Prop. & Applns* 3 331–390 1984.
Kano et al. "Three–Component Complexes of Cyclodextrins. Exciplex Formation in Cyclodextrin Cavity," *J. Inclusion Phenomena* 2 pp. 737–746 1984.
Suzuki et al. "Spectroscopic Investigation of Cyclodextrin Monomers, Derivatives, Polymers and Azo Dyes," *J. Inclusion Phenomena* 2, pp. 715–724 1984.
Abstract of Patent, JA 0222164 (Ricoh KK), Dec. 23, 1983 (Absract).
Abstract of patent, JP 58211426 (Sekisui Plastics KK), Dec. 8, 1983).
Derwent Publications, Ltd., London, EP 0072775 (Ciba Geigy AG), Feb. 23, 1983 (Abstract).
van Beek, H.C.A "Light–Induced Colour Changes in Dyes and Materials" *Color Res. and Appl.* 8 176–181 1983.
Connors, K.A. "Application of a stoichiometric model of cyclodextrin complex formation" *Chemical Abstracts* 98 598 [No. 98:53067g] 1983.
Abstract of Patent, EP 0065617 (IBM Corp.), Dec. 1, 1982 (Abstract).
Derwent Publications Ltd., London, J,A, 0187289 (Honshu Paper Mfg KK), Nov. 17, 1982. (Abstract).

Abstract of Patent, JA 0187289 (Honsho Paper Mfg KK), Nov. 17, 1982 (Abstract).
Abstract of Patent, JA 0185364 (Ricoh KK), Nov. 15, 1982 (Abstract).
Derwent Publications, Ltd., London J5 7139146 (Showa Kako KK) Aug. 27, 1982 (abstract).
Abstract of Patent, JA 0090069 (Canon KK), Jun. 4, 1982 (Abstract).
Derwent Publications, Ltd., London, JA 0061785 (Nippon Senka KK), Apr. 14, 1982 (Abstract).
Fischer, "Submicroscopic contact imaging with visible light by energy transfer" *Appl. Phys. Letter* 40(3) 1982.
Abstract of Patent, JA 0010659 (Canon KK), Jan. 20, 1982 (Abstract).
Abstract of Patent, JA 0010661 (Canon KK), Jan. 20, 1982 (Abstract).
Christen "Carbonylverbindungen: Aldehyde und Ketone," *Grundlagen der Organischen Chemie* 255 1982.
Derwent Publications Ltd., London, J,A, 0155263 (Canon KK), Dec. 1, 1981. (Abstract).
Abstract of Patent, JA 0155263 (Canon KK), Dec. 1, 1981 (Abstract).
Abstract of Patent, JA 0147861 (Canon KK), Nov. 17, 1981 (Abstract).
Derwent Publications Ltd., London, J,A, 0143273 (Canon KK), Nov. 7, 1981. (Abstract).
Abstract of Patent, JP 56143272 (Canon KK), Nov. 7, 1981 (Abstract).
Patent Abstracts of Japan, JP 56143274 (Canon Inc.) Nov. 7, 1981, abstract.
Abstract of Patent, JA 0136861 (Canon KK), Oct. 26, 1981 (Abstract).
Abstract of Patent, JA 6133378 (Canon KK), Oct. 19, 1981 (Abstract).
Abstract of Patent, JA 6133377 (Canon KK), Oct. 19, 1981 (Abstract).
Abstract of Patent, JA 6093775 (Canon KK), Jul. 29, 1981 (Abstract).
Derwent Publications Ltd., London, J,A, 0008135 (Ricoh KK), Jan. 21, 1981. (Abstract).
Derwent Publications Ltd., London, J,A, 0004488 (Canon KK), Jan. 17, 1981 (Abstract).
Abstract of Patent, JA 0004488 (Canon KK), Jan. 17, 1981 (Abstract).
Kirk–Othmer "Metallic Coatings," *Encyclopedia of Chemical Technology* 15 241–274 1981.
Komiyama et al. "One–Pot Preparation of 4–Hydroxychalcone β–Cyclodextrin as Catalyst," *Makromol. Chem.* 2 733–734 1981.
Derwent Publications, Ltd., London CA 1086–719 (Sherwood Medical) Sep. 30, 1980 (abstract).
Derwent Publications Ltd., Database WPI, JP 55 113036 (Ricoh KK), Sep. 1, 1980.
Rosanske et al. "Stoichiometric Model of Cyclodextrin Complex Formation" *Journal of Pharmaceutical Sciences* 69 (5) 564–567 1980.
Semple et al. "Synthesis of Functionalized Tetrahydrofurans," *Tetrahedron Letters* 81 pp. 4561–4564 1980.
Kirk–Othmer "Film Deposition Techniques," *Encyclopedia of Chemical Technology* 10 247–283 1980.
Derwent World Patents Index, Derwent Info. Ltd., JP 54158941 (Toyo Pulp KK), Dec. 15, 1979. (Abstract).
Derwent World Patents Index, JP 54117536 (Kawashima F) Sep. 12, 1979.

Derwent Publications Ltd., London, J,A, 0005422 (Fuji Photo Film KK), Jan. 16, 1979. (Abstract).
Drexhage et al. "Photo–bleachable dyes and processes" *Research Disclosure* 85–87 1979.
"Color imaging devices and color filter arrays using photo–bleachable dyes" *Research Disclosure* 22–23 1979.
Wolff, N.E., et al. "Electrophotography" *Kirk–Othmer Encyclopedia of Chemical Technology* 8 794–826 1979.
Derwent Publications Ltd., London, J,A, 0012037 (Pentel KK), Jan. 29, 1977. (Abstract).
Abstract of Patent, JA 0012037 (Pentel KK), Jan. 29, 1977 (Abstract).
Jenkins, P.W. et al. "Photobleachable dye material" *Research Disclosure* 18 [No. 12932] 1975.
Lamberts, R.L. "Recording color grid patterns with lenticules" *Research Disclosure* 18–19 [No. 12923] 1975.
Karmanova, L.S. et al. "Light stabilizers of daytime fluorescent paints" *Chemical Abstracts* 82 147 [No. 59971p] 1975.
Prokopovich, B. et al. "Selection of effective photoinducers for rapid hardening of polyester varnish PE–250" *Chemical Abstracts* 83 131 [No. 81334a] 1975.
"Variable Contrast Printing System" *Research Disclosure* 19 [No. 12931] 1975.
Lakshman "Electronic Absorption Spectrum of Copper Formate Tetrahydrate" *Chemical Physics Letters* 31 (2) 331–334 1975.
Derwent Publications, Ltd., London J4 9131–226 (TNational Cash Register C) Dec. 16, 1974 (abstract).
Chang, I.F., et al. "Color Modulated Dye Ink Jet Printer" *IBM Technical Disclosure Bulletin* 17(5) 1520–1521 1974.
"Darocur 1173: Liquid Photoiniator for Ultraviolet Curing of Coatings" 1974.
Hosokawa et al. "Ascofuranone, an antibiotic from Ascochyta," Japan Kokai 73 91,278 (Nov. 28, 1973) *MERCK Index* 80 p. 283; abstract 94259t.
Abstract of patent, NL 7112489 (Dec. 27, 1971).
Gafney et al. "Photochemical Reactions of Copper (II)—1, 3–Diketonate Complexes" *Journal of the Americqal Chemical Society* 1971.
Derwent Publications, Ltd., London SU 292698–S Jan. 15, 1971 (abstract).
Derwent World Patents Index,CS 120380 (Kocourek, Jan) Oct. 15, 1966.
Tsuda, K., et al. Vinyl Polymerization. CXLVI. The influence of dibenzoyl disulfide derivatives on radical polymeriations *Chemical Abstract* 196 6:29 198 1966.
Rigdon, J.E. "In Search of Paper that Spies Can't Copy" *Wall Street Journal*.
Chatterjee,S. et al. "Photochemistry of Carbocyanine Alkyltriphenylborate Salts: Intra–Ion–Pair Electron Transfer and the Chemistry of Boranyl Radicals" *J. Am. Chem. Soc.* 112 6329–6338.
"Assay—Physical and Chemical Analysis of Complexes" *AMAIZO*.
"Cyclodextrin" *AMAIZO*.
"Beta Cyclodextrin Polymer (BCDP)" *AMAIZO*.
"Chemically Modified Cyclodextrins" *AMAIZO*.
"Cyclodextrin Complexation" *American Maize Products Co*.
"Monomers" *Scientific Polymer Products Inc.*.
Suppan, Paul "Quenching of Excited States" *Chemistry and Light* 65–69.

Yamaguchi, H. et al. "Supersensitization. Aromatic ketones as supersensitizers" *Chemical Abstracts* 53 107 (d).

Stecher, H. "Ultraviolet–absorptive additives in adhesives, lacquers and plastics" *Chemical Abstracts* 53 14579 (c).

Maslennikov, A.S. "Coupling of diazonium salts with ketones" *Chemical Abstracts* 60 3128e.

Derwent Publications Ltd., London, 4 9128022.

Abstract of Patent, JP 405195450.

Rose, Philip I. "Gelatin," *Encyclopedia of Chemical Technology* 7 488–513.

* cited by examiner

PHOTOINITIATORS AND APPLICATIONS THEREFOR

TECHNICAL FIELD

The present invention relates to novel photoinitiators and methods for generating a reactive species using the photoinitiators. The present invention further relates to methods of polymerizing or photocuring polymerizable material using the above-mentioned photoinitiators. The photoinitiators of the present invention find particular utility in photocurable inks as used in ink jet printers or on a printing press with and without nitrogen blanketing.

BACKGROUND OF THE INVENTION

Polymers have served essential needs in society. For many years, these needs were filled by natural polymers. More recently, synthetic polymers have played an increasingly greater role, particularly since the beginning of the 20th century. Especially useful polymers are those prepared by an addition polymerization mechanism, i.e., free radical chain polymerization of unsaturated monomers, and include, by way of example only, coatings and adhesives. In fact, the majority of commercially significant processes are based on free-radical chemistry. That is, chain polymerization is initiated by a reactive species, which often is a free radical. The source of the free radicals is termed an initiator or photoinitiator.

Improvements in free radical chain polymerization have focused both on (1) more reactive monomer and prepolymer materials and (2) the photoinitiator. Whether a particular unsaturated monomer can be converted to a polymer requires structural, thermodynamic, and kinetic feasibility. Even when all three exist, kinetic feasibility is achieved in many cases only with a specific type of photoinitiator. Moreover, the photoinitiator can have a significant effect on reaction rate which, in turn, may determine the commercial success or failure of a particular polymerization process or product.

A free radical-generating photoinitiator may generate free radicals in several different ways. For example, the thermal, homolytic dissociation of an initiator typically directly yields two free radicals per initiator molecule. A photoinitiator, i.e., an initiator which absorbs light energy, may produce free radicals by one of three pathways:

(1) the photoinitiator undergoes excitation by energy absorption with subsequent decomposition into one or more radicals;

(2) the photoinitiator undergoes excitation and the excited species interacts with a second compound (by either energy transfer or a redox reaction) to form free radicals from the latter and/or former compound(s); or (3) the photoinitiator undergoes an electron transfer to produce a radical cation and a radical anion.

While any free radical chain polymerization process should avoid the presence of species which may prematurely terminate the polymerization reaction, prior photoinitiators present special problems. For example, absorption of the light by the reaction medium may limit the amount of energy available for absorption by the photoinitiator. Also, the often competitive and complex kinetics involved may have an adverse effect on the reaction rate. Moreover, some commercially available radiation sources, such as medium and high pressure mercury and xenon lamps, may emit over a wide wavelength range, thus producing individual emission bands of relatively low intensity. Many photoinitiators only absorb over a small portion of the emission spectra and, as a consequence, much of the lamps' radiation remains unused. In addition, most known photoinitiators have only moderate "quantum yields" (generally less than 0.4) at these wavelengths, indicating that the conversion of light radiation to radical formation can be more efficient.

Many commercially available photoinitiators, including IRGACURE® 369, are presently used in ink compositions to accelerate ink drying in "radiation-drying printing." As used herein, the term "radiation-drying printing" refers to any printing method which utilizes radiation as a drying means. Radiation-drying printing includes, for example, off-set printing operations, such as on a Heidelberg press, flexographic printing, and flat-bed printing. Commercially available photoinitiator systems have a number of shortcomings. First, most of the commercially available photoinitiator systems require a relatively large amount of photoinitiator in the ink composition to fully cure/dry the ink composition. This leads to undesirable extractables within the ink composition. Second, most of the commercially available photoinitiator systems require a hi energy radiation source to induce photocuring. Moreover, even with the high energy radiation source, often the cure results are unsatisfactory. Third, many commercially available photoinitiator systems are highly reactive to oxygen and must be used under a nitrogen blanket. Fourth, even with a large amount of photoinitiator and a high energy light source, the commercially available photoinitiator systems require a dry/cure time only accomplished by multiple passes, as many as 15 passes, under a light source, which significantly limits the output of a radiation-drying printing press.

What is needed in the art is a new class of energy-efficient photoinitiators having unsurpassed photoreactivity even when exposed to a low energy light source, such as a 50 W excimer cold lamp. What is also needed in the art is a new class of energy-efficient photoinitiators that may be cured in air, as well as, a nitrogen atmosphere. Further, what is needed in the art is a class of photoinitiators having unsurpassed photoreactivity, for use in the radiation-drying printing industry, which will significantly increase the output of a radiation-drying printing press due to reduction in ink drying/curing time.

SUMMARY OF THE INVENTION

The present invention addresses some of the difficulties and problems discussed above by the discovery of energy-efficient photoinitiators having the following general formula:

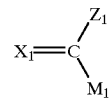

wherein $X_1$ is a conjugated system such as one or more aryl groups or substituted aryl groups; $Z_1$ is —O, —S, an alkyl group having from one to six carbon atoms, an ester moiety, a ketone moiety, an amine moiety, an imine moiety, an ether moiety, an aryl or substituted aryl group, a metal or non-metal, or a metal or non-metal containing group, such as a zinc-containing group or a boron-containing group, respectively; and $M_1$ is an alkyl group, a substituted alkyl group, or forms a five-member ring with $Z_1$. By selecting particular "$X_1$", "$Z_1$", and "$M_1$" groups, photoinitiators are produced having a desired absorption maximum, which substantially corresponds to an emission band of a radiation source and selectively varies from less than about 222 nm to greater than about 445 nm.

The present invention is directed to the above-described photoinitiators, compositions containing the same, and methods for generating a reactive species which includes providing one or more of the photoinitiators and irradiating the one or more photoinitiators. One of the main advantages of the photoinitiators of the present invention is that they efficiently generate one or more reactive species under extremely low energy lamps, such as excimer lamps and mercury lamps, as compared to prior art photoinitiators. The photoinitiators of the present invention also efficiently generate one or more reactive species in air or in a nitrogen atmosphere. Unlike many prior photoinitiators, the photoinitiators of the present invention are not sensitive to oxygen. Further, the photoinitiators of the present invention are as much as ten times faster than the best prior art photoinitiators.

The present invention is further directed to a method of efficiently generating a reactive species by matching a photoinitiator having an absorption maximum to an emission band of a radiation source, which corresponds to the absorption maximum. By adjusting the substituents of the photoinitiator, one can shift the absorption maximum of the photoinitiator from less than about 222 nm to greater than 445 nm.

The present invention is also directed to methods of using the above-described photoinitiators to polymerize and/or photocure a polymerizable material. The photoinitiators of the present invention result in rapid curing times in comparison to the curing times of prior art photoinitiators, even with relatively low output lamps. The present invention includes a method of polymerizing an polymerizable material by exposing the polymerizable material to radiation in the presence of the efficacious wavelength specific photoinitiator composition described above. When an unsaturated oligomer/monomer mixture is employed, curing is accomplished.

The present invention further includes a film and a method for producing a film, by drawing an admixture of polymerizable material and one or more photoinitiators of the present invention, into a film and irradiating the film with an amount of radiation sufficient to polymerize the composition. The admixture may be drawn into a film on a nonwoven web or on a fiber, thereby providing a polymer-coated nonwoven web or fiber, and a method for producing the same.

The present invention is also directed to an adhesive composition comprising a polymerizable material admixed with one or more photoinitiators of the present invention. Similarly, the present invention includes a laminated structure comprising at least two layers bonded together with the above-described adhesive composition, in which at least one layer is a nonwoven web or film. Accordingly, the present invention provides a method of laminating a structure wherein a structure having at least two layers with the above-described adhesive composition between the layers is irradiated to polymerize the adhesive composition.

The present invention is further directed to a method of printing, wherein the method comprises incorporating one or more photoinitiators of the present invention into an ink composition; printing the ink onto a substrate; and drying the ink with a source of radiation.

These and other features and advantages of the present invention will become apparent after a review of the following detailed description of the disclosed embodiments and the appended claims.

DETAILED DESCRIPTION OF THE INVENTION

The present invention is directed to energy-efficient, reactive, photoinitiators and methods for utilizing the same. More particularly, the present invention is directed to new photoinitiators having the following general formula:

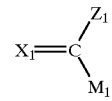

wherein $X_1$ comprises a conjugated system such as one or more aryl groups or substituted aryl groups; $Z_1$ is —O, —S, an alkyl group having from one to six carbon atoms, an ester moiety, a ketone moiety, an amine moiety, an imine moiety, an ether moiety, an aryl or substituted aryl group, a metal or non-metal, or a metal or non-metal containing group, such as a zinc-containing group or a boron-containing group, respectively; and $M_1$ comprises an alkyl group, a substituted alkyl group, or forms a five-member ring with $Z_1$.

The present invention is further directed to a method of efficiently generating a reactive species by matching a photoinitiator having an absorption maximum to an emission band of a radiation source, which corresponds to the absorption maximum. By adjusting the substituents of the photoinitiator, one can shift the absorption maximum of the photoinitiator from less than about 222 nm to greater than 445 nm.

The present invention also includes a method of polymerizing a polymerizable material by exposing the polymerizable material to electromagnetic radiation in the presence of one or more of the photoinitiators described above. Further, the present invention is directed to a film and a method for producing a film, by drawing an admixture of polymerizable material and one or more of the photoinitiators described above, into a film and irradiating the film with an amount of electromagnetic radiation sufficient to polymerize the admixture.

The present invention is further directed to an adhesive composition comprising a polymerizable material admixed and one or more photoinitiators of the present invention. Similarly, the present invention includes a laminated structure comprising at least two layers bonded together with the above-described adhesive composition. The present invention further provides a method of laminating a structure wherein a structure having at least two layers with the above-described adhesive composition between the layers is irradiated with appropriate electromagnetic radiation to polymerize the adhesive composition.

Definitions

As used herein, the term "reactive species" is used herein to mean any chemically reactive species including, but not limited to, free-radicals, cations, anions, nitrenes, and carbenes. Illustrated below are examples of several of such species. Examples of carbenes include, for example, methylene or carbene, dichlorocarbene, diphenylcarbene, alkylcarbonyl-carbenes, siloxycarbenes, and dicarbenes. Examples of nitrenes include, also by way of example, nitrene, alkyl nitrenes, and aryl nitrenes. Cations (sometimes referred to as carbocations or carbonium ions) include, by way of illustration, a proton; primary, secondary, and tertiary alkyl carbocations, such as methyl cation, ethyl cation, propyl cation, t-butyl cation, t-pentyl cation, t-hexyl cation; allylic cations; benzylic cations; aryl cations, such as triphenyl cation; cyclopropylmethyl cations; methoxymethyl cation; triarylsulphonium cations; and acyl cations. Cations also include those formed from various metal salts, such as tetra-n-butylammonium tetrahaloaurate(III) salts; sodium tetrachloroaurate(III); vanadium tetrachloride; and silver, copper(I) and (II), and thallium(I) triflates. Examples of anions (sometimes referred to as carbanions) include, by way of example, alkyl anions, such as ethyl anion, n-propyl anion, isobutyl anion, and neopentyl anion; cycloalkyl anions, such as cydopropyl anion, cyclobutyl anion, and cyclopentyl anion; allylic anions; benzylic anions; aryl cations; and sulfur- or phosphorus-containing alkyl anions. Finally, examples of organometallic photoinitiators include titanocenes, fluorinated diaryltitanocenes, iron arene complexes, manganese decacarbonyl, and methylcyclopentadienyl manganese tricarbonyl. Organometallic photoinitiators generally produce free radicals or cations.

As used herein, the term "quantum yield" is used herein to indicate the efficiency of a photochemical process. More particularly quantum yield is a measure of the probability that a particular molecule will absorb a quantum of light during its interaction with a photon. The term expresses the number of photochemical events per photon absorbed. Thus, quantum yields may vary from zero (no absorption) to 1.

As used herein, the term "polymerization" is used herein to mean the combining, e.g. covalent bonding, of a number of smaller molecules, such as monomers, to form large molecules, i.e., macromolecules or polymers. The monomers may be combined to form only linear macromolecules or they may be combined to form three-dimensional macromolecules, commonly referred to as crosslinked polymers.

As used herein, the term "curing" means the polymerization of functional oligomers and monomers, or even polymers, into a crosslinked polymer network. Thus, curing is the polymerization of unsaturated monomers or oligomers in the presence of crosslinking agents.

As used herein, the terms "unsaturated monomer," "functional oligomer," and "crosslinkng agent" are used herein with their usual meanings and are well understood by those having ordinary skill in the art. The singular form of each is intended to include both the singular and the plural, i.e., one or more of each respective material.

As used herein, the term "unsaturated polymerizable material" is meant to include any unsaturated material capable of undergoing polymerization. The term encompasses unsaturated monomers, oligomers, and crosslinking agents. Again, the singular form of the term is intended to include both the singular and the plural.

As used herein, the term "fiber" as used herein denotes a threadlike structure. The fibers used in the present invention may be any fibers known in the art. As used herein, the term "nonwoven web" as used herein denotes a web-like matter comprised of one or more overlapping or interconnected fibers in a nonwoven manner. It is to be understood that any nonwoven fibers known in the art may be used in the present invention.

Photoinitiators

The present invention is directed to new photoinitiators having the following general formula:

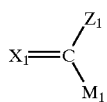

wherein $X_1$ is a conjugated system such as one or more aryl groups or substituted aryl groups; $Z_1$ is —O, —S, an alkyl group having from one to six carbon atoms, an ester moiety, a ketone moiety, an amine moiety, an imine moiety, an ether moiety, an aryl or substituted aryl group, a metal or non-metal, or a metal or non-metal containing group, such as a zinc-containing group or a boron-containing group, respectively; and $M_1$ is an alkyl group, a substituted alkyl group, or forms a five-member ring with $Z_1$. In one embodiment of the present invention, $X_1$ comprises

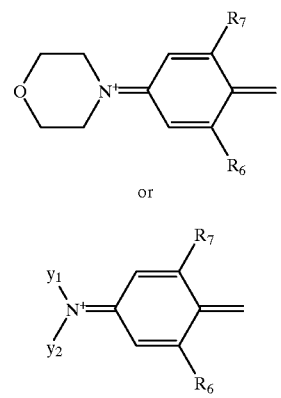

or wherein $R_6$ and $R_7$ each independently represent hydrogen, an alkyl group having from one to six carbon atoms, an alkoxy group having from one to six carbon atoms, or a halogen-substituted alkyl group; and wherein $y_1$ and $y_2$ each independently represent a hydrogen, an alkyl group having from one to six carbon atoms, an aryl group,

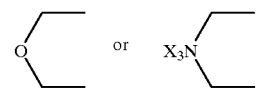

wherein $X_3$ represents a hydrogen, an alkyl or substituted alkyl group, or an aryl or substituted aryl group. Other suitable $X_1$ groups include, but are not limited to, the following:

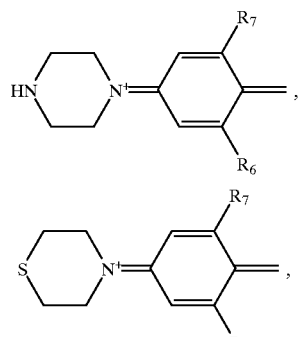

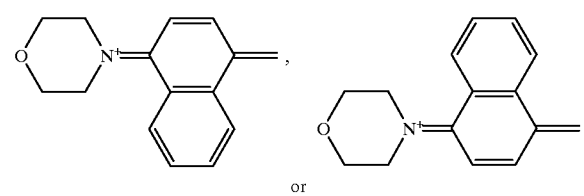

or

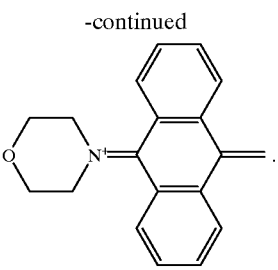

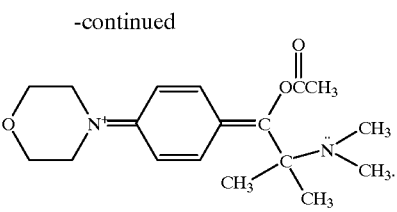

Desirably, $R_6$ and $R_7$ each independently represent a methyl group, an ethyl group, an isopropyl group, a methoxy group, an ethoxy group, or a trifluoromethyl group.

In a further embodiment of the present invention, $M_1$ comprises a tertiary alkyl group having the following formula:

wherein $y_3$, $y_4$ and $y_5$ each independently represent a hydrogen, an alkyl group having from one to six carbon atoms, a tertiary amine group, an aryl group, or a substituted aryl group.

In one embodiment of the present invention, the photoinitiator has the following structure:

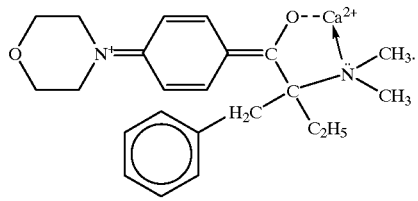

In the above structure, a calcium ion forms a five member ring, which includes the oxygen atom ("$Z_1$") and the electron-rich nitrogen atom. As used herein, an arrow represents a coordinate covalent bond between an electron-rich nitrogen atom and a metal or non-metal cation. It should be understood that other cations may be used instead of the calcium ion. Other suitable cations include, but are not limited to, beryllium, magnesium, strontium, barium, zinc, aluminum, and copper (II).

In a further embodiment, $Z_1$ in the above-described general formula comprises an ester moiety. Examples of such photoinitiators include, but are not limited to, photoinitiators having the following structure:

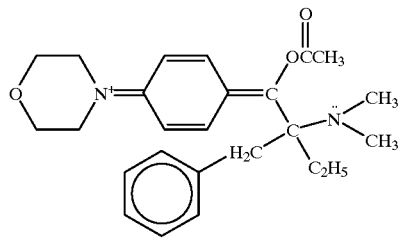

or

In the above photoinitiators, it should be noted that the —C(O)CH$_3$ group ("$Z_1$") may be substituted with other groups including, but not limited to, —CH$_3$, —BF$_3$ and phenyl groups.

In yet a further embodiment, the photoinitiators of the present invention have the following general formula:

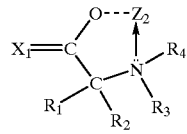

wherein $X_1$ is as defined above; $Z_2$ is a metal or non-metal cation, such as $Zn^{2+}$, $Ca^{2+}$, or boron, or a salt thereof, or —C(O)R, which forms a covalent bond with the oxygen atom; and R, $R_1$, $R_2$, $R_3$, and $R_4$ are each independently a hydrogen atom, an alkyl or substituted alkyl group, or an aryl or substituted aryl group. In a further embodiment, $R_1$ and $R_2$ may form one or more aromatic rings with $X_1$.

Photoinitiators having the above formula include, but are not limited to, the following photoinitiators:

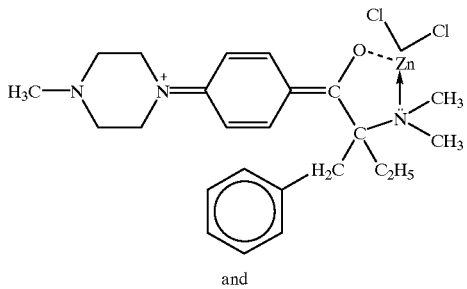

and

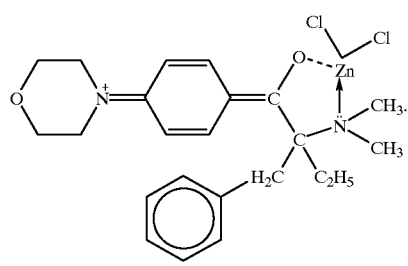

One photoinitiator of particular interest, having the above general formula, is shown below:

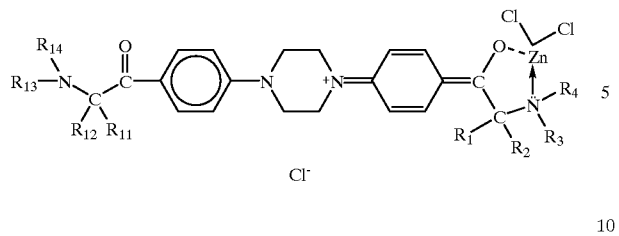

wherein $R_{11}$, $R_{12}$, $R_{13}$, and $R_{14}$ are each independently a hydrogen atom; an alkyl group or substituted alkyl group.

In one embodiment of the present invention, the photoinitiator has the following structure:

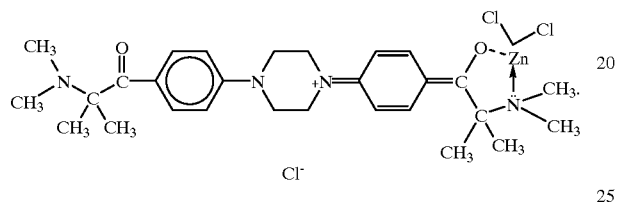

In a further embodiment of the present invention, the photoinitiator has the following structure:

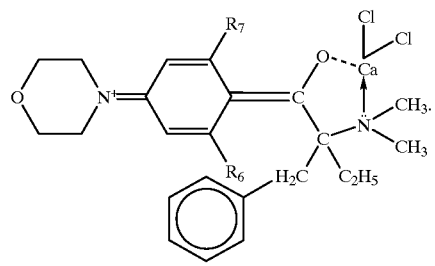

In the above structure, the calcium atom forms a five member ring, which includes the oxygen atom and the electron-rich nitrogen atom. It should be understood that other salts may be used instead of the calcium chloride. Other suitable salts include, but are not limited to, salts containing beryllium, magnesium, strontium, barium, zinc, aluminum, scandium, and copper (II). For example, another photoinitiator of the present invention may have the following structure:

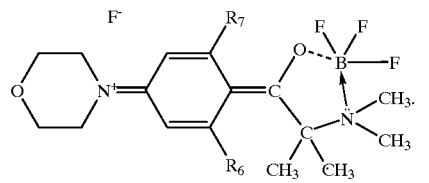

In a further embodiment of the present invention, $R_1$, $R_2$, and $X_1$ of the above-described general formula form one or more aromatic rings to form a photoinitiator having the structure below:

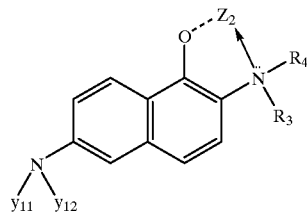

wherein $Z_2$, $R_3$, and $R_4$, are substituents as defined above and $y_{11}$ and $y_{12}$ are each independently represent a hydrogen, an alkyl group having from one to six carbon atoms; an aryl group;

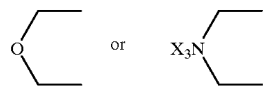

wherein $X_3$ is defined above.

The present invention is further directed to novel photoinitiators having the following general formula:

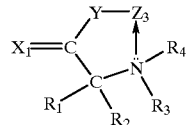

wherein Y is —O— or —N($R_5$)—; $Z_3$ is a metal or nonmetal cation or a salt containing the cation; and $X_1$, $R_1$, $R_2$, $R_3$, $R_4$, and $R_5$ are as defined above. Suitable $Z_3$ groups include, but are not limited to, metals and metal salts containing Cd, Hg, Zn, Al, Ga, In, Tl, Sc, Ge, Pb, Si, Ti, Sn, and Zr, as well as, nonmetals and nonmetal salts containing boron and phosphorus. Desirably, $Z_3$ comprises a chloride-containing salt such as zinc chloride, zinc benzyl chloride, or boron chloride. Desirably, "R" comprises hydrogen, a methyl group, an ethyl group, a propyl group, or a benzyl group.

In one embodiment of the present invention, the photoinitiator has the following structure:

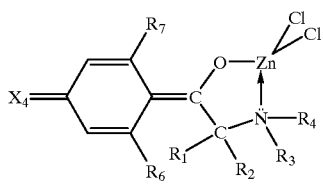

wherein $X_4$ comprises any nitrogen-containing group, which donates a pair of electrons to the nitrogen-carbon double bond; and $R_1$, $R_2$, $R_3$, $R_4$, $R_6$, and $R_7$ are as defined above. The above photoinitiator has an absorption maximum of about 360 nm. In a further embodiment of the present invention, the photoinitiator has the following structure:

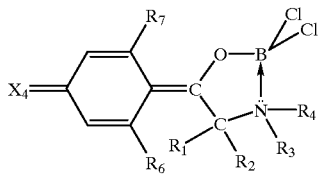

wherein $X_4$, $R_1$, $R_2$, $R_3$, $R_4$, $R_6$, and $R_7$ are as defined above. By replacing the zinc chloride with boron chloride, the absorption maximum of the photoinitiator shifts to about 410 nm.

Other photoinitiators of the present invention have the following structure:

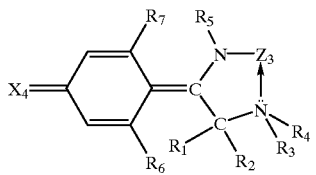

wherein $X_4$, $R_1$, $R_2$, $R_3$, $R_4$, $R_5$, $R_6$, and $R_7$ are as defined above. In one embodiment of the present invention, the photoinitiator has the following structure:

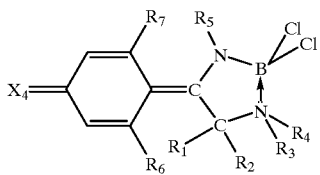

wherein $X_4$, $R_1$, $R_2$, $R_3$, $R_4$, $R_5$, $R_6$, and $R_7$ are as defined above. By replacing the oxygen atom with a nitrogen atom in the five member ring, the absorption maximum of the photoinitiator shifts further to greater than about 410 nm. It should be noted that other metal and nonmetal salts may be used in place of the metal and nonmetal chlorides. For example, the above photoinitiator may have the following structure:

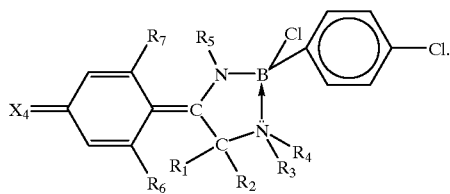

The above-described photoinitiators of the present invention may be produced by the following reaction mechanism:

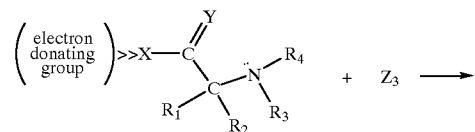

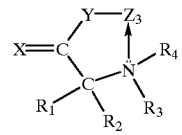

wherein a first compound reacts with a metal or metal salt or a nonmetal or nonmetal salt, $Z_3$, to produce a photoinitiator of the present invention, having a five-member ring containing a metal or nonmetal atom, at least one nitrogen atom, two carbon atoms, and possibly an oxygen atom.

In a further embodiment of the present invention, the photoinitiators have the following general formula:

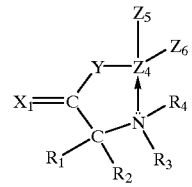

wherein $X_1$, Y, $R_1$, $R_2$, $R_3$, $R_4$, and $R_5$ are as defined above; $Z_4$ is a metal or nonmetal atom; and $Z_5$ and $Z_6$ are halogen-containing anions or form one or more rings with or without $R_3$ or $R_4$. In the above photoinitiator structure, the nitrogen atom donates its lone electron pair to metal or nonmetal atom, $Z_4$, to form a five member ring. Suitable , $Z_4$ groups include, but are not limited to, metals such as Cd, Hg, Zn, Mg, Al, Ga, In, Tl, Sc, Ge, Pb, Si, Ti, Sn and Zr, as well as, nonmetals such as boron and phosphorus. Desirably, $Z_4$ comprises Cd, Zn, Mg, Ti, boron or phosphorus. More desirably, $Z_4$ comprises Zn. Suitable $Z_5$ and $Z_6$ groups include, but are not limited to, halogen-containing anions. Desirably, $Z_5$ and $Z_6$ each independently comprise fluorine, chlorine or bromine-containing anions. More desirably, $Z_5$ and $Z_6$ each independently comprise fluorine-containing anions. Even more desirably, $Z_5$ and $Z_6$ each independently comprise $BF_4$, $AsF_6$, $PF_6$, or $SbF_6$. Desirably, $R_1$, $R_2$, $R_3$, and $R_4$ each independently comprise hydrogen, a methyl group, an ethyl group, a propyl group, or a benzyl group.

In one embodiment of the present invention, the photoinitiator has the following structure:

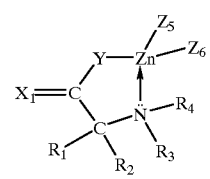

wherein $X_1$, Y, $R_1$, $R_2$, $R_3$, $R_4$, $Z_5$, and $Z_6$ are as defined above. In a further embodiment of the present invention, the photoinitiator has the following structure:

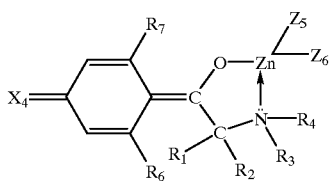

wherein $X_4$, $R_1$, $R_2$, $R_3$, $R_4$, $R_5$, $R_6$, $R_7$, $Z_5$, and $Z_6$ are as defined above. Other photoinitiators of the present invention have the following structure:

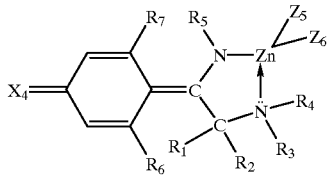

wherein $X_4$, $R_1$, $R_2$, $R_3$, $R_4$, $R_5$, $R_6$, $R_7$, $Z_5$, and $Z_6$ are as defined above.

In yet a further embodiment, the photoinitiator of the present invention has the following structure:

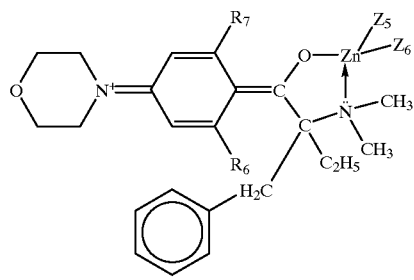

wherein $Z_5$ and $Z_6$ are as defined above. In a further embodiment of the present invention, the photoinitiator of the present invention has the following structure:

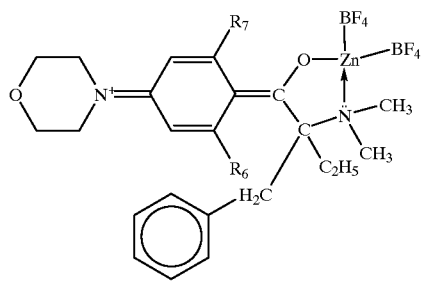

The above-described photoinitiators of the present invention may be produced by the following reaction mechanism:

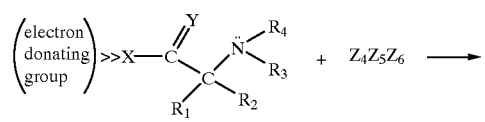

wherein a first compound reacts with a metal or nonmetal salt, $Z_4Z_5Z_6$, to produce a photoinitiator of the present invention, having a five-member ring containing a metal or nonmetal atom, at least one nitrogen atom, two carbon atoms, and possibly an oxygen atom.

The present invention is further directed to novel photoinitiators having the following general structure:

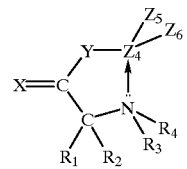

wherein $Y_2$ and $Y_3$ each independently represent —O— or —N($R_3$)($R_4$)—, and $X_1$, $R_1$, $R_2$, $R_3$, $R_4$, $Z_4$, $Z_5$, and $Z_6$ are as defined above. In one embodiment of the present invention, $Y_3$ represents —N($R_3$)($R_4$)— and $Z_5$ and $Z_6$ form two five member rings: one five member ring which includes $Z_4$, $Z_5$, and $Z_6$, and one five member rings which includes with $Z_4$, $Z_6$ and one of $R_3$ or $R_4$. The resulting photoinitiator has the following structure:

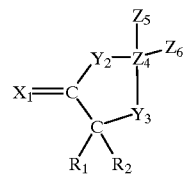

wherein $Z_5$, $Z_6$ and $R_4$ comprise any combination of carbon, nitrogen and oxygen atoms to form two five member rings. It should be noted that $Z_5$, $Z_6$ and $R_4$ may form two similar ring structures or two different ring structures. Also, each ring formed by $Z_5$, $Z_6$ and $R_4$ may contain more than five ring members. In one embodiment of the present invention, the resulting photoinitiator has the following structure:

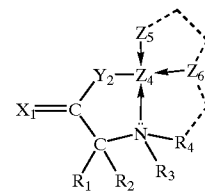

wherein $X_1$, $Y_2$, $R_1$, $R_2$, $R_3$, and $Z_4$ are as defined above; and $n_1$ and $n_2$ each independently represent an integer from 1 to 5. Desirably, the resulting photoinitiator has the following structure:

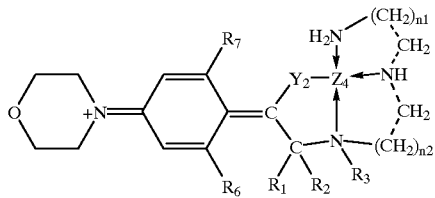

wherein $R_1$, $R_2$, $R_3$, $R_6$, $R_7$, $n_1$, and $n_2$ are as defined above.

In a further embodiment of the present invention, $Z_5$ and $Z_6$ form a single ring. The resulting photoinitiator has the following structure:

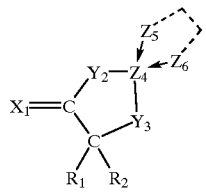

wherein $Z_5$ and $Z_6$ comprise any combination of carbon, nitrogen and oxygen atoms to form a ring. In one embodiment of the present invention, $Z_5$ and $Z_6$ form a five member ring so that the resulting photoinitiator has a dimeric structure. One example of the resulting photoinitiator has the following structure:

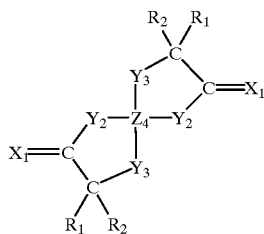

wherein $X_1$, $Y_2$, $Y_3$, $Z_4$, $R_1$ and $R_2$ are as defined above.

Other photoinitiators of the present invention having the above-described structure include, but are not limited to, the following photoinitiators:

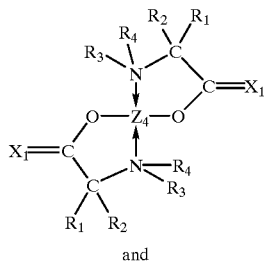

and

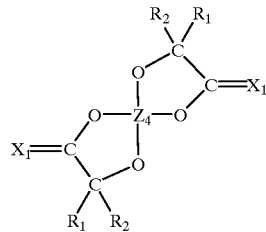

wherein $X_1$, $Z_4$, $R_1$ and $R_2$ are as defined above. Other desirable photoinitiators include, but are not limited to, the following photoinitiators:

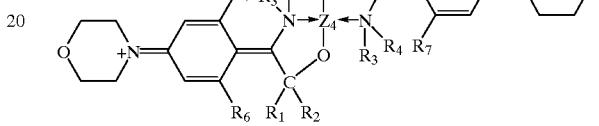

and

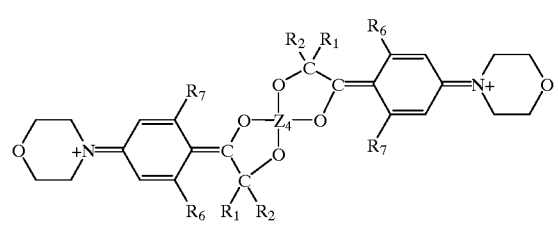

wherein $Z_4$, $R_1$, $R_2$, $R_3$, $R_4$, $R_6$ and $R_7$ are as defined above. Desirably, $Z_4$ comprises boron or zinc in the dimeric structures above. It should be understood that the above dimeric structures are only examples of suitable dimeric structures for the photoinitiators of the present invention. Any combination of "$X_1$", "Z", "Y", and "R" groups may be used to form suitable dimeric structures for the photoinitiators of the present invention.

The resulting photoinitiators are relatively stable at room temperature (from about 15° C. to 25° C.) and normal room humidity (from about 5% to 60%; desirably from 5% to 30%). However, upon exposure to radiation at an appropriate wavelength, the photoinitiators efficiently produce one or more reactive species. The photoinitiators of the present invention have a high intensity of absorption. For example, the photoinitiators of the present invention have a molar extinction coefficient (absorptivity) greater than about 20,000 $1\ mole^{-1}cm^{-1}$. As a further example, the photoinitiators of the present invention have a molar extinction coefficient greater than about 25,000 $1\ mole^{-1}cm^{-1}$.

Method of Generating a Reactive Species and Applications Therefor

The present invention is further directed to a method of generating a reactive species. The method of generating a reactive species involves generating a reactive species by exposing one or more of the above-described photoinitiators to radiation. The exposure of the photoinitiators to a radiation source triggers a photochemical process. As stated above, the term "quantum yield" is used herein to indicate the efficiency of a photochemical process. More particularly, quantum yield is a measure of the probability that a particular molecule (photoinitiator) will absorb a quantum of light during its interaction with a photon. The term expresses the number of photochemical events per photon absorbed. Thus, quantum yields may vary from zero (no absorption) to 1.

The photoinitiators of the present invention absorb photons having a relatively specific wavelength and transfers the absorbed energy to one or more excitable portions of the molecule. The excitable portion of the molecule absorbs enough energy to cause a bond breakage, which generates one or more reactive species. The efficiency with which a reactive species is generated with the photoinitiators of the present invention is significantly greater than that experienced with photoinitiators of the prior art as indicated by faster cure times. For example, the photoinitiators of the present invention desirably will have a quantum yield greater than about 0.8. More desirably, the quantum yield of the photoinitiators of the present invention will be greater than about 0.9. Even more desirably, the quantum yield of the photoinitiators of the present invention will be greater than about 0.95. Still more desirably, the quantum yield of the photoinitiators of the present invention will be greater than about 0.99, with the most desirable quantum yield being about 1.0.

Exposing the photoinitiators of the present invention to radiation results in the generation of one or more reactive species. Thus, the photoinitiators may be employed in any situation where reactive species are required, such as for the polymerization of an unsaturated monomer and the curing of an unsaturated oligomer/monomer mixture. The unsaturated monomers and oligomers may be any of those known to one having ordinary skill in the art. In addition, the polymerization and curing media also may contain other materials as desired, such as pigments, extenders, amine synergists, and such other additives as are well known to those having ordinary skill in the art.

By way of illustration only, examples of unsaturated monomers and oligomers include ethylene, propylene, vinyl chloride, isobutylene, styrene, isoprene, acrylonitrile, acrylic acid, methacylic acid, ethyl acrylate, methyl methacrylate, vinyl acrylate, alkyl methacrylate, tripropylene glycol diacrylate, trimethylol propane ethoxylate acrylate, epoxy acrylates, such as the reaction product of a bisphenol A epoxide with acrylic acid; polyether acrylates, such as the reaction product of acrylic acid with an adipic acid/hexanediol-based polyether, urethane acrylates, such as the reaction product of hydroxypropyl acrylate with diphenylmethane-4,4'-diisocyanate, and polybutadiene diacrylate oligomer.

The types of reactions that various reactive species enter into include, but are not limited to, addition reactions, including polymerization reactions; abstraction reactions; rearrangement reactions; elimination reactions, including decarboxylation reactions; oxidation-reduction (redox) reactions; substitution reactions; and conjugation/deconjugation reactions.

Accordingly, the present invention also comprehends a method of polymerizing a polymerizable material, such as an unsaturated monomer or epoxy compound, by exposing the polymerizable material to radiation in the presence of the effacious photoinitiators of the present invention described above. When an unsaturated oligomer/monomer mixture is employed in place of an unsaturated monomer, curing is accomplished. It is to be understood that the polymerizable material admixed with the photoinitiators of the present invention is to be admixed by means known in the art, and that the mixture will be irradiated with an amount of radiation sufficient to polymerize the material. The amount of radiation sufficient to polymerize the material is readily determinable by one of ordinary skill in the art, and depends upon the identity and amount of photoinitiators, the identity and amount of the polymerizable material, the intensity and wavelength of the radiation, and the duration of exposure to the radiation.

In one embodiment of the present invention, one or more photoinitiators of the present invention are used to polymerize an epoxy resin. It is believed that the following reaction mechanism takes place in the presence of a hydrogen-donating compound, such as an alcohol, cumene or amine:

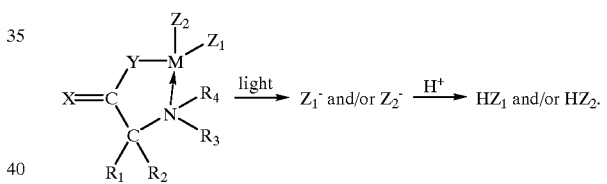

Reactive species, $HZ_1$ and/or $HZ_2$, then react with an epoxy resin according to the following mechanism to produce a polyether:

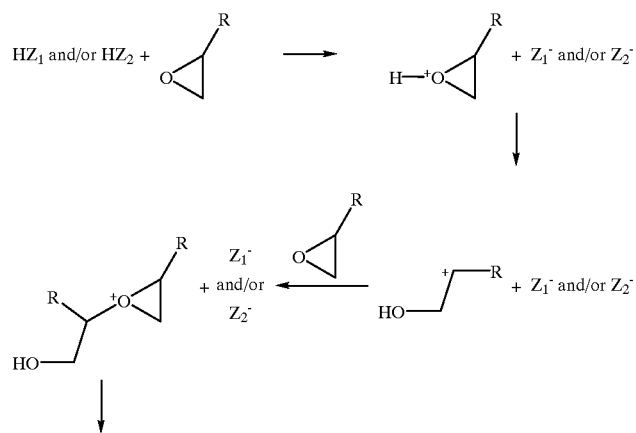

-continued

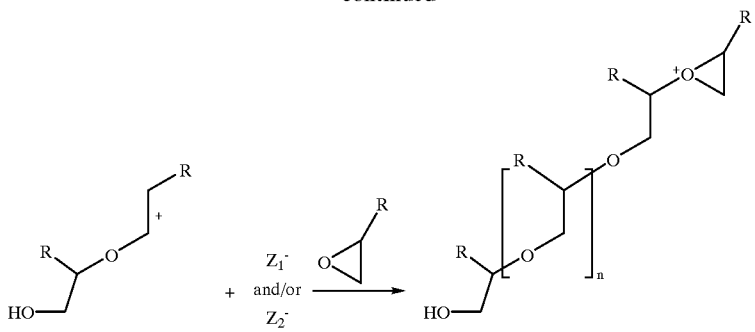

The weak conjugate bases, $Z_1^-$ and/or $Z_2^-$, which are non-nueophilic, enable the polymerization reaction to take place, unlike other anions, which may prematurely terminate the polymerization reaction.

Polymer Films, Coated Fibers and Webs, and Adhesive Compositions

The present invention further includes a film and a method for producing a film, by drawing an admixture of a polymerizable material and one or more photoinitiators of the present invention, into a film and irradiating the film with an amount of radiation sufficient to polymerize the composition. When the polymerizable material is an unsaturated oligomer/monomer mixture, curing is accomplished. Any film thickness may be produced, as per the thickness of the admixture formed, so long as the admixture sufficiently polymerizes upon exposure to radiation. The admixture may be drawn into a film on a nonwoven web or on a fiber, thereby providing a polymer-coated nonwoven web or fiber, and a method for producing the same. Any method known in the art of drawing the admixture into a film may be used in the present invention. The amount of radiation sufficient to polymerize the material is readily determinable by one of ordinary skill in the art, and depends upon the identity and amount of photoinitiator, the identity and amount of the polymerizable material, the thickness of the admixture, the intensity and wavelength of the radiation, and duration of exposure to the radiation.

The present invention also includes an adhesive composition comprising a polymerizable material admixed with one or more photoinitiators of the present invention. Similarly, the present invention includes a laminated structure comprising at least two layers bonded together with the above-described adhesive composition. In one embodiment of the present invention, a laminate is produced wherein at least one layer is a cellulosic or polyolefin nonwoven web or film. Accordingly, the present invention provides a method of laminating a structure wherein a structure having at least two layers with the above-described adhesive composition between the layers is irradiated to polymerize the adhesive composition. When the unsaturated polymerizable material in the adhesive is an unsaturated oligomer/monomer mixture, the adhesive is irradiated to cure the composition.

It is to be understood that any layers may be used in the laminates of the present invention, on the condition that at least one of the layers allows sufficient radiation to penetrate through the layer to enable the admixture to polymerize sufficiently. Accordingly, any cellulosic or polyolefin nonwoven web or film known in the art may be used as one of the layers so long as they allow radiation to pass through. Again, the amount of radiation sufficient to polymerize the admixture is readily determinable by one of ordinary skill in the art, and depends upon the identity and amount of photoinitiator, the identity and amount of the polymerizable material, the thickness of the admixture, the identity and thickness of the layer, the intensity and wavelength of the radiation, and the duration of exposure to the radiation.

The radiation to which the photoinitiators of the present invention may be exposed generally will have a wavelength of from about 4 to about 1,000 nanometers. Thus, the radiation may be ultraviolet radiation, including near ultraviolet and far or vacuum ultraviolet radiation; visible radiation; and near infrared radiation. Desirably, the radiation will have a wavelength of from about 100 to about 900 nanometers. More desirably, the radiation will have a wavelength of from about 100 to 700 nanometers. Desirably, the radiation will be ultraviolet radiation having a wavelength of from about 4 to about 400 nanometers. More desirably, the radiation will have a wavelength of from about 100 to about 420 nanometers, and even more desirably will have a wavelength of from 320 to about 420 nanometers. The radiation desirably will be incoherent, pulsed ultraviolet radiation from a dielectric barrier discharge excimer lamp or radiation from a mercury lamp.

Excimers are unstable excited-state molecular complexes which occur only under extreme conditions, such as those temporarily existing in special types of gas discharge. Typical examples are the molecular bonds between two rare gaseous atoms or between a rare gas atom and a halogen atom. Excimer complexes dissociate within less than a microsecond and, while they are dissociating, release their binding energy in the form of ultraviolet radiation. The dielectric barrier excimers in general emit in the range of from about 125 nm to about 500 nm, depending upon the excimer gas mixture.

Dielectric barrier discharge excimer lamps (also referred to hereinafter as "excimer lamp") are described, for example, by U. Kogelschatz, "Silent discharges for the generation of ultraviolet and vacuum ultraviolet excimer radiation." Pure & Appl Chem., 62, No. 9, pp. 1667–1674 (1990); and E. Eliasson and U. Kogelschatz, "UV Excimer Radiation from Dielectric- Barrier Discharges." Appl. Phys. B. 46, pp. 299–303 (1988). Excimer lamps were developed by ABB Infocom Ltd., Lenzburg, Switzerland, and at the present time are available from Heraeus Noblelight GmbH, Kleinostheim, Germany.

The excimer lamp emits incoherent, pulsed ultraviolet radiation. Such radiation has a relatively narrow bandwidth, i.e., the half width is of the order of approximately 5 to 100 nanometers. Desirably, the radiation will have a half width of the order of approximately 5 to 50 nanometers, and more desirably will have a half width of the order of 5 to 25 nanometers. Most desirably, the half width will be of the order of approximately 5 to 15 nanometers.

The ultraviolet radiation emitted from an excimer lamp can be emitted in a plurality of wavelengths, wherein one or more of the wavelengths within the band are emitted at a maximum intensity. Accordingly, a plot of the wavelengths in the band against the intensity for each wavelength in the band produces a bell curve. The "half width" of the range of ultraviolet radiation emitted by an excimer lamp is defined as the width of the bell curve at 50% of the maximum height of the bell curve.

The emitted radiation of an excimer lamp is incoherent and pulsed, the frequency of the pulses being dependent upon the frequency of the alternating current power supply which typically is in the range of from about 20 to about 300 kHz. An excimer lamp typically is identified or referred to by the wavelength at which the maximum intensity of the radiation occurs, which convention is followed throughout this specification and the claims. Thus, in comparison with most other commercially useful sources of ultraviolet radiation which typically emit over the entire ultraviolet spectrum and even into the visible region, excimer lamp radiation is essentially monochromatic.

Although excimer lamps are highly desirable for use in the present invention, the source of radiation used with the photoinitiators of the present invention may be any radiation source known to those of ordinary skill in the art. In a further embodiment of the present invention, a mercury lamp with a D-bulb, which produces radiation having an emission peak of about 360 nm is used to produce free radicals from the above-described photoinitiators. This radiation source is particularly useful when matched with one or more photoinitiators of the present invention having an absorption maximum of about 360 nanometers, corresponding to the emission peak of the mercury lamp. Other specialty doped lamps, which emit radiation at about 420 nm, may be used with photoinitiators of the present invention which have an absorption maximum at about 420 nm. One lamp, the V-bulb available from Fusion Systems, is another suitable lamp for use in the present invention. In addition, specialty lamps having a specific emission band may be manufactured for use with one or more specific photoinitiators of the present invention. New lamp technology provides the following potential advantages:

(a) substantially single wavelength output;
(b) unique wavelength output;
(c) high intensity; and
(d) absence of radiation trapping.

As a result of the photoinitiators of the present invention absorbing radiation in the range of about 250 to about 390 nanometers, some of the photoinitiators of the present invention will generate one or more reactive species upon exposure to sunlight. Accordingly, these photoinitiators of the present invention provides a method for the generation of reactive species that does not require the presence of a special light source.

The photoinitiators of the present invention enable the production of adhesive and coating compositions that consumers can apply to a desired object and polymerize or cure upon exposure to sunlight. These photoinitiators also enable numerous industry applications wherein polymerizable materials may be polymerized merely upon exposure to sunlight. Therefore, depending upon how the photoinitiator is designed, the photoinitiator of the present invention can eliminate the cost of purchasing and maintaining light sources in numerous industries wherein such light sources are necessary without the photoinitiators of the present invention.

The effective tuning of the photoinitiators of the present invention for a specific wavelength band permits the photoinitiators of the present invention to more efficiently utilize the target radiation in the emission spectrum of the radiating source corresponding to the "tuned" wavelength band, even though the intensity of such radiation may be much lower than, for example, radiation from a narrow band emitter, such as an excimer lamp. For example, it may be desirable to utilize an excimer lamp, or other radiation emission source, that emits radiation having a wavelength of approximately 360 nm or 420 nm with the photoinitiators of the present invention. However, the effectiveness of the photoinitiators of the present invention is not necessarily dependent upon the availability or use of a narrow wavelength band radiation source.

Use of the Above-Described Photoinitiators in an Ink Composition

The above-described photoinitiators of the present invention may be incorporated into ink compositions. In one embodiment of the present invention, one or more of the photoinitiators are incorporated into an ink jet ink composition for use on ink jet ink printers. The ink composition may be used on commercially available ink jet printing machines alone or in combination with a radiation source in series with the ink jet printing machine for instantaneous curing of the ink jet ink composition. Any radiation source known to those of ordinary skill in the art may be used to cure the ink jet ink composition. Desirably, one of the above-described radiation sources is used to cure the ink composition.

Use of the Above-Described Photoinitiators in Other Radiation-Drying Printing Process A further use of the above-described photoinitiators of the present invention involves the incorporation of one or more of the photoinitiators into an ink composition for use on a radiation-drying printing press. As discussed above, "radiation-drying printing" refers to any printing method which utilizes radiation as a drying means. Radiation-drying printing includes, for example, off-set printing operations, such as on a Heidelberg press, flexographic printing, and flat-bed printing.

The photoinitiators of the present invention enable increased press output due to the photoreactivity of the photoinitiators. Further, the increased output may be obtained while using a minimal amount of photoinitiator and a low energy light source. In one embodiment of the present invention, complete curing at an output rate of 10,000 printed sheets per hour may be obtained using a 50 W cold lamp as the light source.

Any of the above-described photoinitiators may be used in the printing processes disclosed herein. Desirably, the amount of photoinitiator added to the ink composition, adhesive composition or resin is less than about 4.0 wt % of the total weight of the composition. More desirably, the amount of photoinitiator added to the composition is from about 0.25 to about 3.0 wt % of the total weight of the composition. Most desirably, the amount of photoinitiator added to the composition is from about 0.25 to about 2.0 wt % of the total weight of the composition.

A major advantage of the photoinitiators of the present invention is that they enable rapid curing times of ink compositions, adhesive compositions and/or resins in comparison to the curing times of prior art photoinitiators. Ink compositions containing the photoinitiators of the present invention possess rapid curing times from 5–10 times faster than the curing times of ink compositions containing the best known photoinitiators. The use of the photoinitiators of the present invention in ink compositions, adhesive compositions or resins for printing presses enables print speeds, which were at one time thought to be unobtainable. For example, in an open air printing process using a Heidelberg print press and a 50 W excimer cold lamp for photocuring, desirably the printed sheet output is greater than 6,000 sheets per hour. More desirably, the printed sheet output is greater than 8,000 sheets per hour. Most desirably, the printed sheet output is greater than 10,000 sheets per hour.

The present invention is further described by the examples which follow. Such examples, however, are not to be construed as limiting in any way either the spirit or the scope of the present invention. In the examples, all parts are by weight, unless stated otherwise.

COMPARATIVE EXAMPLE 1

Photocuring of CGI 369 in Red Flexo Resin

A mixture of Ciba Geigy photoinitiator 369 (CGI 369) in the form of a powder was added to a 1 g sample of red flexo ink (Gamma Graphics). The mixture was exposed to UV radiation while positioned within an FTIR machine to monitor the decrease in carbon-carbon double bonds within the mixture. The curing rate was measured.

EXAMPLE 1

Photocuring of One of KC's New Photoinitiators in Red Flexo Resin

A mixture of Kimberly Clark's photoinitiator, having the following structure, in the form of a powder was added to a 1 g sample of red flexo ink (Gamma Graphics).

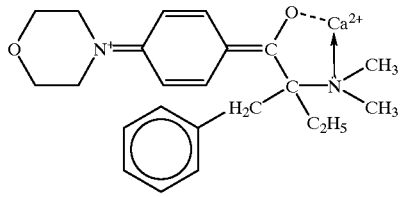

The mixture was exposed to UV radiation while positioned within an FTIR machine to monitor the decrease in carbon-carbon double bonds within the mixture. The curing rate was measured. The photoinitiator had a curing rate relative to the CGI 369 photoinitiator of greater than 220%.

EXAMPLE 2

Method of Forming a 1-(p-fluorophenyl)-2-dimethylamine-ethanone Intermediate to a Photoinitiator of the Present Invention The following reaction was carried out as detailed below:

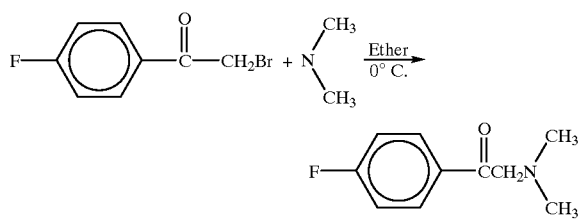

Into a three-necked round-bottom flask was placed 200 ml of anhydrous diethyl ether with stirrer bar and bubbler inlet. The ether was cooled to 0° C. Dimethyl amine was bubbled into the solvent for 1 hour to make a saturated solution. Into the flask was placed 10.0 g (0.046 mole) of 1-p-fluorophenacyl bromide dissolved in 50 ml of ether over a period of about 20 minutes. The temperature of the mixture was kept at 0° C. for about 4 hours and then allowed to raise to room temperature overnight. The reaction mixture was then filtered to remove the dimethyl amine hydroxide and the solvent to yield a yellow oil. The oil was pumped in a vacuum oven and used in further examples without further purification. The final product was 1-(p-fluorophenyl)-2-dimethylamine-ethanone and the yield of the reaction was 7.5 g of oil (94%).

EXAMPLE 3

Method of Forming a 1-(p-fluorophenyl)-2-dimethylamine-2-methyl-propanone Intermediate to a Photoinitiator of the Present Invention The following reaction was carried out as detailed below:

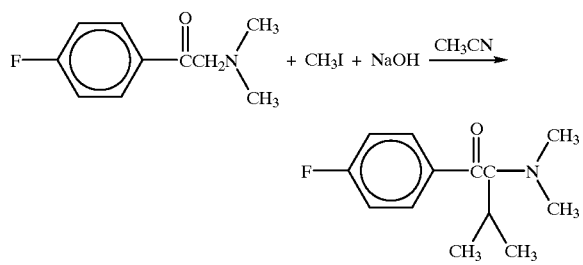

Into a 1-liter, round-bottom flask was placed 5.0 g (0.028 mole) of the 1-(p-fluorophenyl)-2-dimethylamine-ethanone compound of Example 1, 8.6 g (0.062 mole) of methyl iodide, and 330 ml of acetonitrile. The reaction mixture was stirred for about 4 hours. The solvent was then removed and replaced with 300 ml of water and 7.3 g of a 34 wt % solution of sodium hydroxide (0.07 mole). The reaction mixture was then heated at about 55° C. to 60° C. for about 1 hour. On cooling, the reaction mixture was extracted with ether, and dried over magnesium sulfate. The solvent was removed under reduced pressure to yield an oil which was pumped in the vacuum oven. The product crystallized in a refrigerator overnight. The final product was measured to be 4.1 g of 1-(p-fluorophenyl)-2-dimethylamine-2-methyl-propanone and the yield was found to be about 71%.

EXAMPLE 4

Method of Forming a Piperazine-Containing Intermediate to a Photoinitiator of the Present Invention The following reaction was carried out as detailed below:

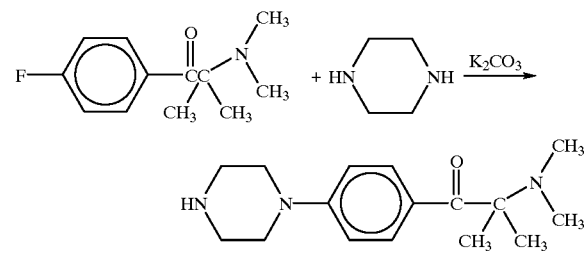

Into a 250 ml, round-bottom flask was placed 1.4 g (0.01 mole) of potassium carbonate, 2.0 g of the product from Example 2, 0.86 g (0.01 mole) of piperazine, and 20 ml of N,N-dimethylformamide (DMF). The mixture was flushed with argon for about 20 minutes prior to heating at reflux. The reaction mixture was heated at reflux for about 16 hours. HPLC indicated a 80% conversion to the desired product shown below (This was the only compound having a 325 nm UV absorption peak.) The crude product was recrystallized from ethanol to yield a pale yellow solid. The yield of the reaction was 1.8 g of 1-piperazine-2-dimethylamine-2-methyl-propanone (69%).

EXAMPLE 5

Method of Forming a Zn-Containing Photoinitiator of the Present Invention

The following reaction was carried out as detailed below:

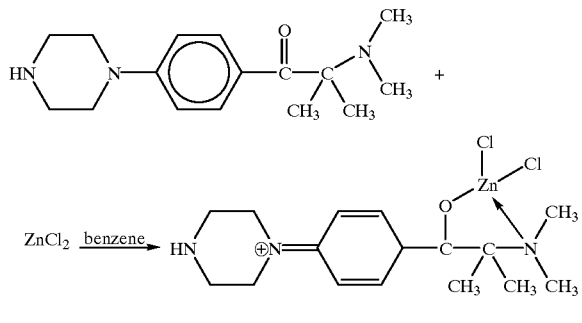

In order to form one of the photoinitiators of the present invention, zinc chloride containing water was heated under an argon gas atmosphere to produce zinc chloride free of water. Into a 250 ml, three-necked, round-bottom flask fitted with condenser, argon gas inlet, and bubbler outlet was placed 2.6 g ( 0.019 mole) of $ZnCl_2$. The flask was continuously flushed with argon while the $ZnCl_2$ was heated with a propane torch. The $ZnCl_2$ was heated for about 15 minutes until it melted. Heating was continued for about ten minutes and then the $ZnCl_2$ was allowed to cool under an argon atmosphere. The product was ground to form a powder, still under an argon atmosphere.

The resulting $ZnCl_2$, 80 ml of benzene, and 8 g of the 1-morpholino-2-dimethylamine-2-methyl-propanone produced in Example 4 were heated at reflux for about 12 hours in an argon atmosphere. The solution was then cooled and filtered. The solvent was removed under reduced pressure to yield a yellow powder. The powder was pumped in a vacuum oven at ambient temperature to yield 6.9 g of photoinitiator (yield 79%) having the structure above.

Samples of the yellow solid were mixed into offset black resins (GERBER-SCHMIDT GmbH, Frankfurt, Germany) at 2.0 wt % based on the total weight of the resin. The resins were drawn down into a thin film and exposed to an excimer lamp (308 nm). The resins fully cured after 1–2 flashes (0.05 seconds/flash). The control prepared with IRGACURE® 369 (available from Ciba Geigy) took 6–8 flashes and was still not fully cured.

EXAMPLE 6

Method of Forming a New Zn-Containing Photoinitiator

In order to form one of the photoinitiators of the present invention, zinc chloride containing water was heated under an argon gas atmosphere to produce zinc chloride free of water. Into a 1-liter, three-necked flask was placed 7.4 g ( 0.05 mole) of $ZnCl_2$. The flask was continuously flushed with argon while the $ZnCl_2$ was heated with a propane torch. The $ZnCl_2$ was heated until it liquified. Heating was continued for about ten minutes and then the $ZnCl_2$ was allowed to cool. The product was ground to form a powder, still under an argon atmosphere.

The resulting $ZnCl_2$, 200 ml of benzene, and 20 g (0.05 mole) of IRGACURE® 369 (available from Ciba Geigy) having the following structure

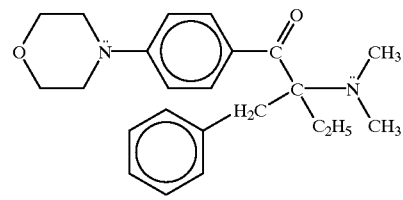

were heated at reflux for about 12 hours in an argon atmosphere. The solution was then cooled and filtered. The solvent was removed under reduced pressure.

The resulting modified-369 compound had the following structure:

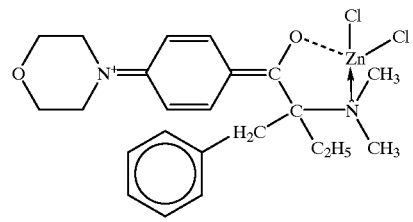

The yellow solid was found to have a similar retention time and UV absorption compared to IRGACURE® 369. However, the cure rate of a resin containing the yellow solid was 3 to 5 times faster than the cure rate of an identical resin containing the IRGACURE® 369 photoinitiator.

Samples of the yellow solid were mixed into offset and flexo resins (GERBER-SCHMIDT GmbH, Frankfurt, Germany) at 2.0 and 3.0 wt % based on the total weight of the resin. The resins were printed onto white plates and exposed to an excimer lamp (308 nm) or a mercury lamp (360 nm). The resins rapidly cured.

EXAMPLE 7

Method of Forming a New $BF_3$-Containing Photoinitiator

Into a 1-liter, three-necked flask was placed 100 g (0.275 mole) of IRGACURE® 369 and 500 ml of dry benzene. The flask was continuously flushed with argon and cooled in an ice bath. Into the flask was added 38.8 g (0.0275 mole) of boron trifluoride etherate. The reaction was carried out in the dark and stirred at 0° C. for about 10 hours.

A yellow precipitate formed and was filtered. The solvent was removed under reduced pressure to yield 82.1 g (69% yield) of a yellow solid.

HPLC indicated a different retention time and a UV absorption at about 415 nm.

Samples of the yellow solid were mixed into offset and flexo resins at 2.0 and 3.0 wt % based on the total weight of the resin. The resins were rapidly cured when printed onto white plates and exposed to a Fusion Systems 'V' Bulb (420 nm).

EXAMPLE 8

Method of Forming a New BCl$_3$-Containing Photoinitiator

Into a 1-liter, three-necked flask was placed 10 g (0.027 mole) of IRGACURE® 369 and 50 ml of dry benzene. The flask was continuously flushed with argon and cooled in an ice bath. Into the flask was added 3.16 g (0.027 mole) of boron trichloride in xylene. The reaction was stirred overnight at 0° C. for about 10 hours.

A yellow precipitate formed and was filtered. The solvent was removed under reduced pressure to yield 11.2 g (86% yield) of a yellow solid.

HPLC indicated a retention time and a UV absorption similar to IRGACURE® 369.

Samples of the yellow solid were mixed into offset resins at 2.0 wt % based on the total weight of the resin. The resins were rapidly cured when drawn down onto white plates and exposed to an excimer lamp (308 nm).

EXAMPLE 9

Offset Printing Using Photoinitiators of the Present Invention

Two lots of Zn-containing photoinitiator were prepared as in Examples 2–5 above. The lots were designated Z1029 and Z106. Offset printing trials were performed at the Institute for Surface Modification (Leipzig, Germany) using Gerber Schmidt highly pigmented black ink compositions.

The photoinitiator was added to the ink composition and mixed using a high speed vortex mixer. After mixing for about 15 minutes, the temperature was measured to be about 60° C. Similar ink compositions were prepared using IRGACURE® 369.

A sheet-fed offset press manufactured by Heidelberg Press, Model No. GT052, was used to print sheets using the above ink compositions. The press ran up to 8,000 sheets per hour. The curing took place in a nitrogen atmosphere or in 10 air. The results of the printing test are given below in Table 1.

TABLE 1

Cure Results of Offset Printing

| Photoinitiator | Observations |
| --- | --- |
| 4.0 wt % PI 369 | Resin was soft. 95% cured. |
| 4.0 wt % PI 369*** | Resin was soft, poorly cured. |
| 1.0 wt % PI 369 | Resin was very poor, even wet. |
| 4.0 wt % Z1029 | Resin was poor. 70 to 80% cured. |
| 3.0 wt % Z1029 | Resin was better, but still soft. 80% cured. |
| 2.0 wt % Z1029 | Resin was even better. 85% cured. |
| 1.0 wt % Z1029 | Resin was better than the PI 369. 90% cured. |
| 0.75 wt % Z1029 and 0.25 wt % PI 369 | Good surface cure, but soft under the surface. |
| 1.0 wt % Z1029 and 0.25 wt % PI 369*** | Good surface cure. 95% cured. |
| 1.0 wt % Z1029 and 0.25 wt % PI 369*** | Good surface cure. 95% cured. |
| 1.0 wt % Z1029 and 0.5 wt % PI 369 | Hard surface cure. 100% cured. |
| 1.0 wt % Z1029 and 0.5 wt % PI 369*** | Good surface cure. 95% cured. |
| 1.0 wt % Z1029 and 0.5 wt % PI 369 | Hard solid cure. 100% cured. |
| 1.0 wt % Z1029 and 0.5 wt % PI 369 | Good surface cure. Soft under the surface. 90% cured. |
| 1.0 wt % Z1029 and 0.75 wt % PI 369 | Hard solid cure. 100% cured. |
| 1.0 wt % Z1029 and 0.75 wt % PI 369*** | Good surface cure. Good cure under the surface. 98% cured. |
| 1.0 wt % Z1029 and 1.0 wt % PI 369 | Hard solid cure. 100% cured. |
| 1.0 wt % Z1029 and 1.0 wt % PI 136*** | Good surface cure. Good cure under the surface. 96% cured. |

***Test was run in air, as opposed to a nitrogen atmosphere.

As shown in Table 1, photoinitiator systems of the present invention consistently provided better cure than IRGACURE® 369 alone. The photoinitiators of the present invention provided good cure results in a nitrogen atmosphere, as well as, in air.

EXAMPLE 10

Method of Forming a New Cationic Photoinitiator

In order to form one of the photoinitiators of the present invention, zinc tetrafluoroborate (available from Aldrich) was heated overnight at 50° C. in a vacuum oven (0.01 mm Hg) to produce zinc tetrafluoroborate free of water. The dried solid and ether were mixed to form a 0.5M solution of zinc tetrafluoroborate in ether.

Four grams (0.01 mole) of IRGACURE® 369 (available from Ciba Geigy) having the following structure

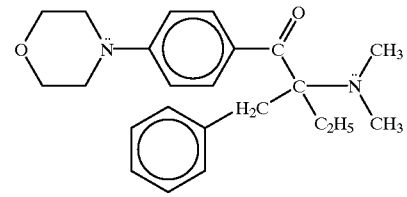

was dissolved in 100 ml of ether (anhydrous) in a three-necked round bottom flask fitted with stirrer bar, argon gas bubbler, and condenser. To this solution was added, via a syringe, 21.5 ml of the 0.5M Zn(BF$_4$)$_2$ ether solution over 10 minutes. The clear solution turned cloudy. A white precipitate formed over a period of an hour. The white precipitate was filtered on a Buckner funnel and washed with 100 ml of anhydrous ether. The powder was then pumped in a vacuum for over an hour at room temperature.

The resulting compound had the following structure:

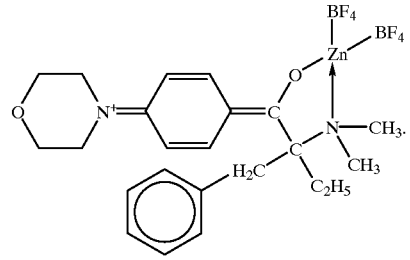

EXAMPLE 11

Curing Process Using a Cationic Photoinitiator

In a beaker 8.5 g of CYRACURE® UVR-6110 (cycloaliphatic diepoxide, available from Union Carbide)

was heated to 50° C. while stirring with a magnetic stirrer. Into the beaker was added 0.1 g of the photoinitiator produced from Example 1, which was allowed to dissolved over a period of 2 minutes. Into the beaker, 2.5 g of UCAR-VAGH (vinyl chloride-vinyl acetate-vinyl alcohol terpolymer, available from Union Carbide) was slowly added while stirring resulting in a clear solution after about 3 minutes.

A drop of the mixture was drawn down onto a metal plate. The film was exposed to a medium pressure mercury arc lamp. The film immediately went from being tacky to fully cured.

EXAMPLE 12

Method of Forming a 1-(2,6-dimethoxy-4-fluorophenyl)-2-methylpropan-1-one Intermediate to a Photoinitiator of the Present Invention The following reaction was carried out as detailed below:

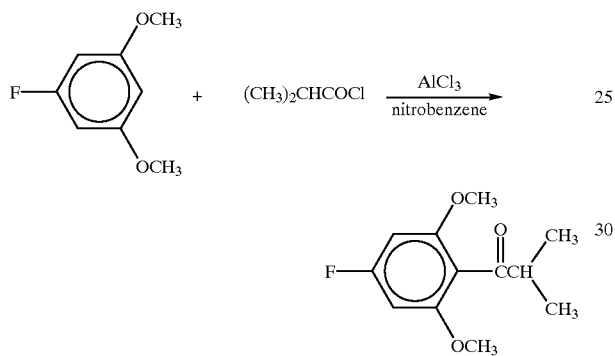

Into a 1-liter, three-necked round-bottom flask was placed 20.0 g (0.13 mole) of 1,3-dimethoxy-5-fluorobenzene, 13.6 g (0.0.13 mole) of 2-methylpropanoyl chloride, and 100 ml of nitrobenzene. The mixture was flushed with argon and an equal molar amount of $AlCl_3$ (17.2 g) was added to the reaction mixture while stirring at 5° C. The mixture was stirred at a temperature of 5° C. for about 1 hour after the addition of the $AlCl_3$. The reaction mixture was then mixed with about 100 ml of distilled water and extracted with dichloromethane. The organic layer was washed with $NaHCO_3$ solution, salt water, and then dried. The solvent was removed by vacuum to yield the final product, 1-(2,6-dimethoxy-4-fluorophenyl)-2-methylpropan-1-one. The yield of the reaction was 22.8 g of product (77%).

EXAMPLE 13

Method of Forming a Morpholino-Containing Intermediate to a Photoinitiator of the Present Invention The following reaction was carried out as detailed below:

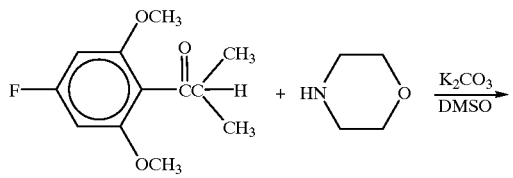

-continued

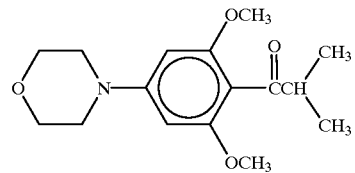

Into a 1-liter, three-necked round-bottom flask was placed 15.0 g (0.07 mole) of 1-(2,6-dimethoxy-4-fluorophenyl)-2-methylpropan-1-one produced in Example 12, 5.8 g (0.07 mole) of morpholine, and 19.0 g (0.14 mole) of $K_2CO_3$ in 100 ml. of dimethylsulfoxide (DMSO). The mixture was flushed with argon and heated to reflux overnight. The reaction mixture was cooled and then mixed with about 100 ml of distilled water and extracted with dichloromethane. The organic layer was washed with $NaHCO_3$ solution, salt water, and then dried. The solvent was removed by vacuum to yield the final product, 1-(2,6-dimethoxy-4-morpholinophenyl)-2-methylpropan-1-one. The yield of the reaction was 18.1 g of product (88%).

EXAMPLE 14

Method of Forming a Morpholino-Containing Bromide Salt Intermediate to a Photoinitiator of the Present Invention The following reaction was carried out as detailed below:

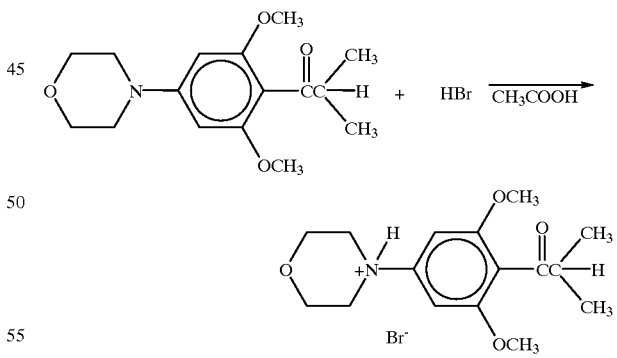

Into a 1-liter, three-necked round-bottom flask was placed 15.0 g (0.05 mole) of 1-(2,6-dimethoxy-4-morpholinophenyl)-2-methylpropan-1-one produced in Example 13 and 150 ml. of glacial acetic acid. Hydrogen bromide gas was bubbled through the mixture for about 40 minutes. The product was then used in the next step, disclosed in Example 15.

EXAMPLE 15

Method of Forming a Morpholino-Containing Bromide-Containing Salt Intermediate to a Photoinitiator of the Present Invention The following reaction was carried out as detailed below:

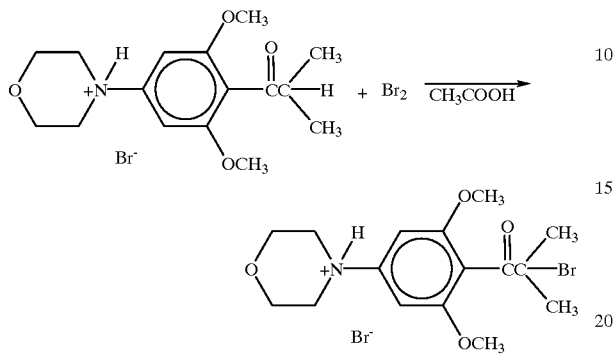

Into a 1-liter, three-necked round-bottom flask was placed 19.1 g (0.05 mole) of the product produced in Example 14. The mixture was chilled to 5° C. To the chilled mixture was added dropwise 8.0 g of $Br_2$ over a period of about one hour. The mixture was then stirred for about one hour. The solvent was removed under vacuum to yield a pale yellow/orange solid. The yield of the final product was 20.9 g of product (92%).

EXAMPLE 16

Method of Forming a Morpholino-Containing Bromide-Containing Salt Intermediate to a Photoinitiator of the Present Invention The following reaction was carried out as detailed below:

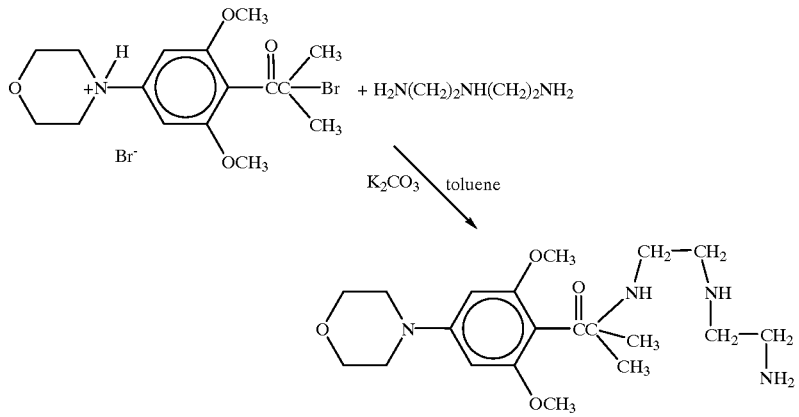

Into a 1-liter, three-necked round-bottom flask was placed 15.0 g (0.03 mole) of the product produced in Example 17, 3.1 g (0.03 mole) of diethylenetriamine, 8.2 g (0.06 mole) of $K_2CO_3$, and 100 ml. of toluene. The mixture was heated at reflux overnight. The solvent was removed under vacuum to yield a yellow solid. The yield of the final product was 8.7 g of product (74%).

EXAMPLE 17

Method of Forming a Zn-complex Photoinitiator of the Present Invention

The following reaction was carried out as detailed below:

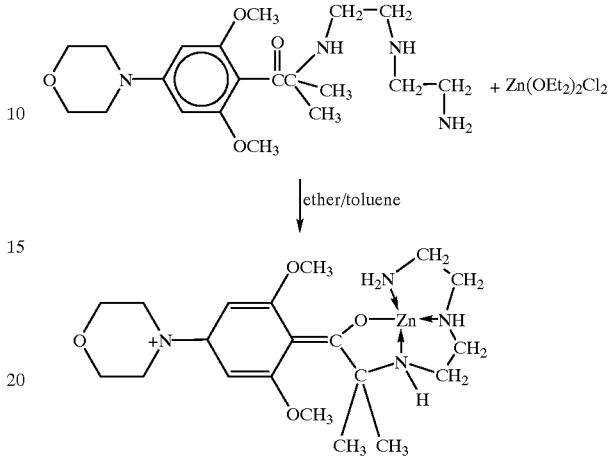

Into a 1-liter, three-necked round-bottom flask was placed 5.0 g (0.013 mole) of the product produced in Example 18 and 50 ml. of toluene. To the mixture was slowly added 1.72 g (0.013 mole) of $Zn(OEt_2)_2Cl_2$ in ether (i.e., 21 ml. of a 0.6M solution of $Zn(OEt_2)_2Cl_2$ in ether). The reaction materials were stored for about one hour at room temperature. The solvent was removed under vacuum to yield a yellow solid. The yield of the final product was 5.4 g of product (96%).

EXAMPLE 18

Testing of Zn-Containing Photoinitiator of the Present Invention in a Red Flexographic Resin A sample containing 0.1 g of the photoinitiator produced in Example 19 and 1.0 g of a red flexographic resin was prepared. A drop of the resin sample was drawn down on a white panel. The thin film was exposed to a 50W excimer lamp (308 nm). The resin fully cured after 4 flashes (0.01 seconds/flash).

While the specification has been described in detail with respect to specific embodiments thereof, it will be appreciated that those skilled in the art, upon attaining an understanding of the foregoing, may readily conceive of alterations to, variations of, and equivalents to these

What is claimed is:

1. A photoinitiator having the following formula:

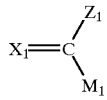

wherein $X_1$ comprises a conjugated system of one or more aryl groups or substituted aryl groups; $Z_1$ comprises —O, —S, an alkyl group having from one to six carbon atoms, an ester moiety, a ketone moiety, an amine moiety, an imine moiety, an ether moiety, an aryl or substituted aryl group, a metal or non-metal, or a metal or non-metal containing group; and $M_1$ comprises an alkyl group, a substituted alkyl group, or forms a five-member ring with $Z_1$.

2. The photoinitiator of claim 1, wherein $X_1$ comprises

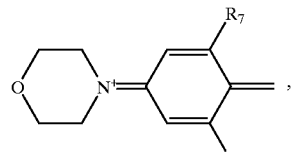

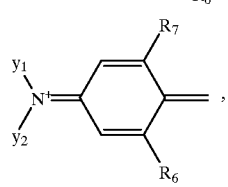

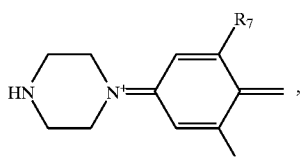

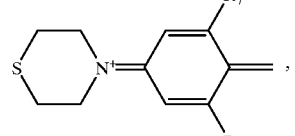

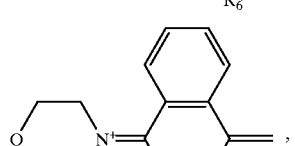

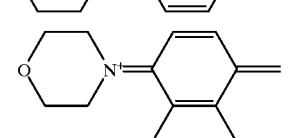

or

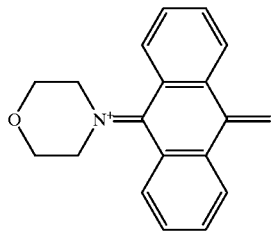

wherein $R_6$ and $R_7$ each independently represent hydrogen, an alkyl group having from one to six carbon atoms, an alkoxy group having from one to six carbon atoms, or a halogen-substituted alkyl group; and wherein $y_1$ and $y_2$ each independently represent a hydrogen, an alkyl group having from one to six carbon atoms, an aryl group,

or

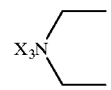

wherein $X_3$ represents a hydrogen, an alkyl or substituted alkyl group, or an aryl or substituted aryl group.

3. The photoinitiator of claim 1, wherein $M_1$ comprises a tertiary alkyl group having the following formula:

wherein $y_3$, $y_4$ and $y_5$ each independently represent a hydrogen, an alkyl group having from one to six carbon atoms, a tertiary amine group, an aryl group, or a substituted aryl group.

4. The photoinitiator of claim 1, wherein $M_1$ and $Z_1$ form a five-member ring.

5. The photoinitiator of claim 4, wherein the photoinitiator has the following structure:

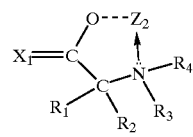

wherein $Z_2$ is a metal or non-metal atom, a metal or non-metal containing salt, or —C(O)R, which forms a covalent bond with the oxygen atom; R, $R_3$ and $R_4$ are each independently a hydrogen atom, an alkyl or substituted alkyl group, or an aryl or substituted aryl group; and $R_1$ and $R_2$ are each independently a hydrogen atom, an alkyl or substituted alkyl group, or an aryl or substituted aryl group, or form one or more aromatic rings with $X_1$.

6. The photoinitiator of claim 5, wherein $R_1$, $R_2$, and $X_1$ form a photoinitiator having the structure below:

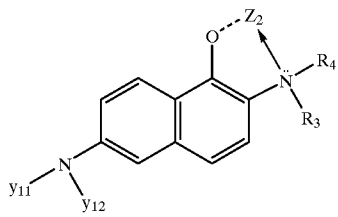

wherein $y_{11}$ and $y_{12}$ are each independently represent a hydrogen, an alkyl group having from one to six carbon atoms, an aryl group,

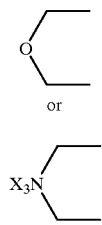

wherein $X_3$ represents a hydrogen, an alkyl or substituted alkyl group, or an aryl or substituted aryl group.

7. The photoinitiator of claim 5, wherein the photoinitiator comprises

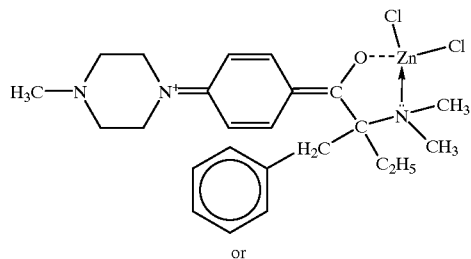

or

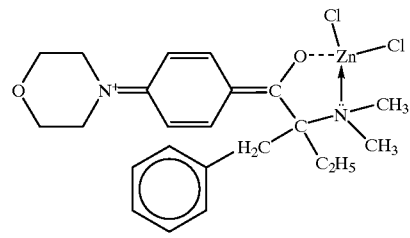

or

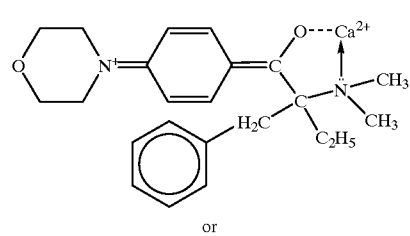

or

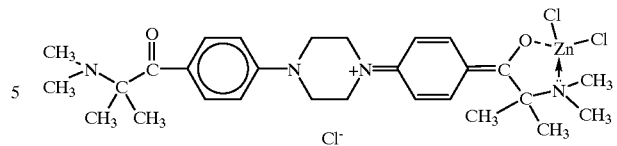

8. The photoinitiator of claim 4, wherein the photoinitiator has the following structure:

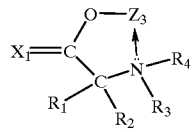

wherein Y is —O— or —N($R_5$)—; $Z_3$ is a metal or nonmetal cation or a salt containing the cation; $R_3$ and $R_4$ are each independently a hydrogen atom, an alkyl or substituted alkyl group, or an aryl or substituted aryl group; and $R_1$ and $R_2$ are each independently a hydrogen atom, an alkyl or substituted alkyl group, or an aryl or substituted aryl group, or form one or more aromatic rings with $X_1$.

9. The photoinitiator of claim 4, wherein the photoinitiator has the following structure:

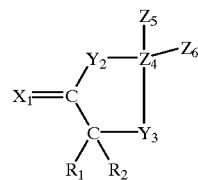

wherein $Y_2$ and $Y_3$ each independently represent —O— or —N($R_3$)($R_4$)—; $R_3$ and $R_4$ are each independently a hydrogen atom, an alkyl or substituted alkyl group, or an aryl or substituted aryl group; $R_1$ and $R_2$ are each independently a hydrogen atom, an alkyl or substituted alkyl group, or an aryl or substituted aryl group or form one or more aromatic rings with $X_1$; $Z_4$ is a metal or nonmetal atom; and $Z_5$ and $Z_6$ are halogen-containing anions or form one or more rings with or without $R_3$ or $R_4$.

10. The photoinitiator of claim 9, wherein $Z_4$ comprises Cd, Hg, Zn, Mg, Al, Ga, In, Tl, Sc, Ge, Pb, Si, Ti, Sn, Zr, boron or phosphorus.

11. The photoinitiator of claim 9, wherein $Z_5$ and $Z_6$ each independently comprise fluorine, chlorine or bromine-containing anions.

12. The photoinitiator of claim 9, wherein the photointiator comprises

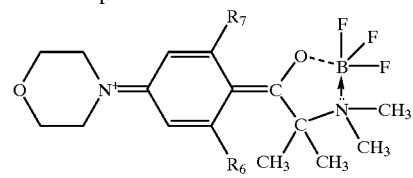

wherein $R_6$ and $R_7$ each independently represent hydrogen, an alkyl group having from one to six carbon atoms, an alkoxy group having from one to six carbon atoms, or a halogen-substituted alkyl group.

13. The photoinitiator of claim 9, wherein the photoinitiator has the following structure:

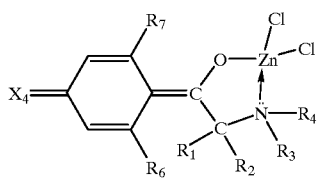

wherein $X_4$ comprises any nitrogen-containing group, which donates a pair of electrons to the nitrogen-carbon double bond; and $R_6$ and $R_7$ each independently represent hydrogen, an alkyl group having from one to six carbon atoms, an alkoxy group having from one to six carbon atoms, or a halogen-substituted alkyl group.

14. The photoinitiator of claim 8, wherein the photoinitiator has the following structure:

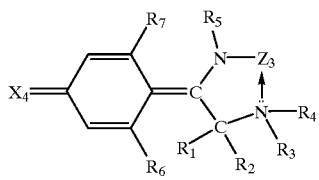

wherein $X_4$ comprises any nitrogen-containing group, which donates a pair of electrons to the nitrogen-carbon double bond; and $R_6$ and $R_7$ each independently represent hydrogen, an alkyl group having from one to six carbon atoms, an alkoxy group having from one to six carbon atoms, or a halogen-substituted alkyl group.

15. The photoinitiator of claim 9, wherein the photoinitiator has the following structure:

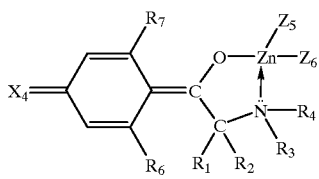

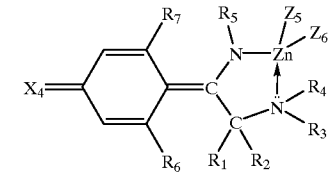

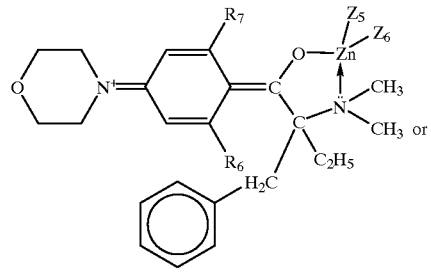

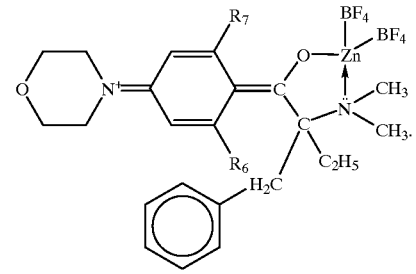

16. A method of generating a reactive species, comprising:

irradiating the cationic photoinitiator of claim 1 with radiation.

17. A method of polymerizing a polymerizable material, comprising:

irradiating an admixture of a polymerizable material and the photoinitiator of claim 1.

* * * * *

UNITED STATES PATENT AND TRADEMARK OFFICE
CERTIFICATE OF CORRECTION

Page 1 of 1

PATENT NO.        : 6,265,458 B1
APPLICATION NO.   : 09/407007
DATED             : July 24, 2001
INVENTOR(S)       : Ronald S. Nohr et al.

It is certified that error appears in the above-identified patent and that said Letters Patent is hereby corrected as shown below:

Title Page, after Filed: Sep. 28, 1999, insert

-- Related U.S. Application Data

Provisional application Nos. 60/102,153, filed on Sep. 28, 1998 and 60/111,950, filed on Dec. 11, 1998 and 60/121,302, filed on Feb. 23, 1999 and 60/124,939, filed on Mar. 18, 1999 and 60/132,630, filed on May 5, 1999. --

Signed and Sealed this
Eighteenth Day of December, 2012

David J. Kappos
*Director of the United States Patent and Trademark Office*